(12) United States Patent
Beattie et al.

(10) Patent No.: US 6,268,147 B1
(45) Date of Patent: Jul. 31, 2001

(54) NUCLEIC ACID ANALYSIS USING SEQUENCE-TARGETED TANDEM HYBRIDIZATION

(76) Inventors: Kenneth Loren Beattie, 1326 Open Range Rd., Crossville, TN (US) 38555; Rogelio Maldonado Rodriguez, Cerrada Merced de las Huertas #28, Mexico, 11420 D. F. (MX)

( * ) Notice: Subject to any disclaimer, the term of this patent is extended or adjusted under 35 U.S.C. 154(b) by 0 days.

(21) Appl. No.: 09/432,020

(22) Filed: Nov. 2, 1999

Related U.S. Application Data

(60) Provisional application No. 60/106,555, filed on Nov. 2, 1998, now abandoned.

(51) Int. Cl.[7] .......................... C12Q 1/68; G01N 33/53; C12M 1/00; C07K 1/00; C07H 21/02
(52) U.S. Cl. .......................... 435/6; 435/7.1; 435/283.1; 435/285.2; 435/286.5; 530/351; 536/23.1
(58) Field of Search ................ 435/6, 7.1, 283.1, 435/285.2, 286.5; 530/350; 536/23.1

(56) References Cited

U.S. PATENT DOCUMENTS 5,804,384 * 9/1998 Muller et al. ............................ 435/6

* cited by examiner

*Primary Examiner*—John S. Brusca
*Assistant Examiner*—Stephen Siu
(74) *Attorney, Agent, or Firm*—Benjamin Aaron Adler

(57) ABSTRACT

The disclosed invention provides a novel method for analyzing genomic DNA and expressed sequences using auxiliary oligonucleotides, preannealed to the single-stranded target nucleic acid to form a partially duplex target molecule, offers several advantages in the analysis of nucleic acid sequences by hybridization to genosensor arrays or "DNA chips". Also provided is a method for directly analyzing and comparing patterns of gene expression at the level of transcription in different cellular samples.

23 Claims, 17 Drawing Sheets

Fig. 8A

```
AGATACAGAAGCGTCATCAAAGCATGCCAACTAGAAGAGG    CF179
CFW13   @cgcagtaGTTTCGTACGGTTGATCTTCTCC    CF164

7654321*
```

| PROBE | SEQ (3'->5') | MISMATCH TYPE | POSITION FROM 5'-END* OF CAPTURE PROBE |
|---|---|---|---|
| CF195 | @cgcagtt | t•t | 1 (terminal mismatch) |
| CF196 | @cgcagtc | t•c | 1 |
| CF197 | @cgcagtg | t•g | 1 |
| CF198 | @cgcagaa | a•a | 2 (one from end) |
| CF199 | @cgcagca | a•c | 2 |
| CF200 | @cgcagga | a•g | 2 |
| CF201 | @cgcaata | c•a | 3 (two from end) |
| CF202 | @cgcacta | c•c | 3 |
| CF203 | @cgcatta | c•t | 3 |
| CF204 | @cgccgta | t•c | 4 (three from end) |
| CF205 | @cgcggta | t•g | 4 |
| CF206 | @cgctgta | t•t | 4 |
| CF207 | @cggagta | g•g | 5 (four from end) |
| CF208 | @cgtagta | g•t | 5 |
| CF209 | @cgaagta | g•a | 5 |

Fig. 12A

NUCLEIC ACID ANALYSIS USING SEQUENCE-TARGETED TANDEM HYBRIDIZATION

CROSS-REFERENCE TO RELATED APPLICATION

This patent application claims benefit of priority of provisional application U.S. Ser. No. 60/106,555, filed Nov. 2, 1998, now abandoned.

BACKGROUND OF THE INVENTION

1. Field of the Invention

The present invention relates generally to the fields of molecular biology and nucleic acid analysis. More specifically, the present invention relates to a novel method of nucleic acid analysis using tandem hybridization approaches.

2. Description of the Related Art

The emerging field of DNA technology is bringing powerful analytical capabilities in research and clinical laboratories. A prime example is the identification of mutations causing genetic diseases, such as the detection of ΔF508 mutation responsible of cystic fibrosis disease (Riordan et al, *Science* 245:1066–1073, 1989). Many technical approaches have been devised to search for the presence of one or a few mutations in a single assay. However, it is now evident that many genetic diseases can be caused by a wide variety of mutations in the gene altered, as with cystic fibrosis, where more than 200 different mutations in the CFTR gene have been detected in CF patients (Tsui, *Trends Genet.* 8:392–398, 1992). Several analytical approaches have recently been proposed to simultaneously investigate multiple mutations in a single assay. For example, fluorescently labeled allele-specific oligonucleotides have been used in the analysis of several mutations by PCR (Heller, In *The Polymerase Chain Reaction*, Mullis et al, Eds., Birkhäusen, Boston, pp. 134–141, 1994) or the ligase chain reaction (Jou et al, *Human Mutat.* 5:86–93, 1995; Eggerdin, *Human Mutat.* 5:153–165, 1995). Oligonucleotide hybridization shows promise as a rapid and sensitive method for simultaneous analysis of large numbers of mutations (Conner et al, *Proc. Natl. Acad. Sci., USA.* 80:278–282, 1983; Southern, International patent application PCT GB 89/00460, 1988; Beattie et al, *Clin. Chem.* 39:719–722, 1992; Southern et al, Genomics 13:1008–1017, 1992; Maskos & Southern, *Nucl. Acids Res.* 20:1675–1678, 1992; Mirzabekov, *Trends Biotechnol.* 12:27–32, 1994; Case-Green et al, In *Innovation and Perspectives in Solid Phase Synthesis, Proc. 3rd International Symposium on Solid Phase Synthesis*, Epton, Ed., Mayflower Worldwide Ltd., Birmingham, U.K., pp. 77–82, 1994; Pease et al, *Proc. Natl. Acad. Sci., U.S.A.* 91:5022–5026, 1994; Nikiforov et al, *Nucl. Acids Res.* 22:4167–4175, 1994; Beattie et al, *Molec. Biotechnol.* 4:213–225, 1995; Beattie et al, *Clin. Chem.* 41:700–706, 1995; Parinov et al, *Nucl. Acids Res.* 24:2998–3004, 1996; Yershov et al, *Proc. Natl. Acad. Sci., U.S.A.* 93:4913–4918, 1996; Hacia et al, *Nature Genetics* 14:441–447, 1996; Southern, *Trends Genet.* 12:110–115, 1996). Various strategies have been described which enable simultaneous analysis of numerous oligonucleotide hybridization reactions. The most common strategy employed to separately analyze the hybridization of numerous oligonucleotide probes to a nucleic acid analyte is to immobilize each oligonucleotide at a specific, addressable site on a surface, then to label the analyte nucleic acid, hybridize it to the oligonucleotide array, and measure the relative quantity of label bound at each position across the array, using a CCD imaging system, a scanning confocal microscope, phosphorimager, exposure of X-ray film, etc. The inverse situation to the use of oligonucleotide arrays to analyze a nucleic acid sample is to immobilize numerous nucleic acid samples in a two-dimensional array, then to analyze the binding of a DNA probe to each of the arrayed analytes. Included in the latter approach are membrane hybridizations using size-separated nucleic acid fragments (as in Southern blots and Northern blots) and slot blots and dot blots in which each analyte is placed onto the membrane at a specific location. In addition, high density arrays of genomic clones, cDNAs, gene-specific amplicons or other PCR products, immobilized onto membranes or onto glass or silicon surfaces, are frequently used in hybridizations with oligonucleotide probes or longer nucleic acid fragments, for genome mapping, genotyping and gene expression profiling. Another approach to multiplex DNA hybridization is to immobilize each DNA probe to microbeads color-coded with a specific "signature" of fluorophores, then to hybridize the analyte nucleic acid labeled with a molecular tag with the bead mixture and analyze the mixture by flow cytometry, using the fluorescent signature to resolve each probe and the molecular tag to quantitate the binding of analyte to each probe (FlowMetrix method of Luminex, Inc.).

Simultaneous hybridization of a DNA sample to numerous oligonucleotide probes attached to a solid support material ("DNA chip," or "genosensor") has been proposed as a powerful research tool in various kinds of DNA sequence analysis, including sequencing by hybridization, scanning for known or unknown mutations in a gene of known nucleotide sequence, genotyping of organisms, and genome mapping (Southern, International patent application PCT GB 89/00460, 1988; Beattie et al, *Clin. Chem.* 39:719–722, 1992; Southern et al, *Genomics* 13:1008–1017, 1992; Maskos & Southern, *Nucl. Acids Res.* 20:1675–1678, 1992; Mirzabekov, *Trends Biotechnol.* 12:27–32, 1994; Case-Green et al, In *Innovation and Perspectives in Solid Phase Synthesis, Proc. 3rd International Symposium on Solid Phase Synthesis*, Epton, Ed., Mayflower Worldwide Ltd., Birmingham, U.K., pp. 77–82, 1994; Pease et al, *Proc. Natl. Acad. Sci., U.S.A.* 91:5022–5026, 1994; Nikiforov et al, *Nucl. Acids Res.* 22:4167–4175, 1994; Beattie et al, *Molec. Biotechnol.* 4:213–225, 1995; Beattie et al, *Clin. Chem.* 41:700–706, 1995; Parinov et al, *Nucl. Acids Res.* 24:2998–3004, 1996; Yershov et al, *Proc. Natl. Acad. Sci., U.S.A.* 93:4913–4918, 1996; Hacia et al, *Nature Genetics* 14:441–447, 1996; Southern, *Trends Genet.* 12:110–115, 1996; Bains & Smith, *J. Theor. Biol.* 135:303–307, 1988; Drmanac et al, *Genomics* 4:114–128, 1989; Khrapko et al, *FEBS Lett.* 256:118–122, 1989; Khrapko et al, *DNA Sequence* 1:375–388, 1991; Bains, *Genomics* 11:294–301, 1991; Fodor et al, *Science* 251:767–773, 1991; Drmanac & Crkvenjakov, *Int. J. Genome Res.* 1:59–79, 1992; Drmanac et al, *Science* 260:1649–1652, 1993; Bains, *DNA Sequence* 4:143–150, 1993; Meier-Ewert et al, *Nature* 361:375–376, 1993; Broude et al, *Proc. Natl. Acad. Sci., USA* 91:3072–3076, 1994; Hoheisel, *Trends Genet.* 10:79–83, 1994; Drmanac & Drmanac, *BioTechniques* 17:328–336, 1994; Lamture et al, *Nucl. Acids Res.* 22:2121–25, 1994; Caetano-Anolles, *Nature Biotechnol.* 14:1668–1674, 1996; Lockhart et al, *Nature Biotechnol.* 14:1675–1680, 1996; Milner et al, *Nature Biotechnol.* 15:537–541, 1997). Despite widespread interest generated about the various multiplex hybridization technologies, several technical challenges remain to be solved before these techniques can reach their full potential and be successfully implemented in a robust fashion. One problem, anticipated from the beginning, is the spontaneous formation of secondary structure in the single stranded target nucleic acid, making certain stretches of target sequence poorly accessible to hybridization (Case-Green et al, In *Innovation and Perspectives in Solid Phase Synthesis, Proc. 3rd International Symposium on Solid Phase Synthesis*, Epton, Ed., Mayflower Worldwide Ltd., Birmingham, U.K., pp. 77–82, 1994; Beattie et al, *Clin. Chem.* 41:700–706, 1995; Milner et al, *Nature Biotechnol.* 15:537–541, 1997). This problem may be especially difficult when short oligonucleotide probes are used, wherein the hybridization temperature is too low to disrupt some regions of intrastrand secondary structure. Many applications of membrane-, chip- or bead-based hybridization technologies, especially those requiring base mismatch discrimination, may require short probes. One strategy for minimizing the secondary or higher order structure in the DNA target is to fragment the target sequence to very small size. However, such cleavage is difficult to control and does not solve the problem in the case of strong hairpin loops occurring within a short target sequence. The strategy of converting the DNA target to RNA (Hacia et al, *Nature Genetics* 14:441–447, 1996), which forms a more stable duplex structure with short oligodeoxynucleotide probes than the original DNA target, may also minimize the problem of secondary structure. The RNA targets can be cleaved to short pieces using 25 mM $MgCl_2$ at 95° C. The procedure used to generate RNA targets from DNA samples, however, is rather cumbersome. Similarly, the use of peptide nucleic acid (PNA) probes, which form even more stable duplex structures with DNA than the RNA•DNA hybrids cited above (Egholm et al, *Nature* 365:556–568, 1993) may help solve the secondary structure problem. PNA is expensive, however, and the stabilizing effect is not uniform over all sequences, and furthermore, the discrimination against mismatches appears to be sacrificed in some sequences using PNA probes (Weiler et al, *Nucl. Acids Res.* 25:2792–2799, 1997).

A further inconvenience in hybridization-based nucleic acid analysis is the need to prepare isolated single-stranded target DNA prior to hybridization to surface-immobilized probes, in order to achieve optimal hybridization signals. Various procedures for isolation of single-stranded targets are available, including the use of affinity columns and strand-specific nuclease digestion, but these added steps are costly, time consuming and inconvenient.

An additional inconvenience in array hybridization analysis is the need to label each nucleic acid analyte prior to hybridization to the DNA probe array. A number of techniques are available for introduction of labels or tags into nucleic acid strands, including (i) the enzymatic incorporation of label from γ-labeled ATP into the 5'-terminus of DNA fragments, using polynucleotide kinase; (ii) incorporation of labeled nucleotides into the target nucleic acid by a polymerase in a "nick translation" or "random primer" labeling reaction, in an in vitro transcription reaction, or in a "reverse transcriptase" reaction; and (iii) direct chemical labeling of DNA or RNA, involving covalent reactions which incorporate fluorescent tags, ligands or haptens into the nucleobases. Although these labeling strategies are straight forward and widely practiced, they nevertheless require additional steps, and if a large number of samples need to be analyzed, the additional labeling steps can be time consuming and expensive. Another problem associated with traditional approaches to sample labeling, especially with complex nucleic acid analytes, is the requirement to introduce a sufficient density of label into the analyte nucleic acid, such that the specific fragment being analyzed is likely to contain at least one label. This can be a problem if the analyte is fragmented prior to hybridization. Furthermore, if a complex mixture of nucleic acid fragments is labeled, nonspecific binding of noncomplementary labeled strands to the array and the occurrence of imperfect hybridization (involving mismatched hybrids) can be a significant problem, since a very small fraction of label will be present on the specific fragment that is complementary to any given immobilized probe.

Another limitation to sequence-targeted nucleic acid analysis by oligonucleotide array hybridization, especially problematic when short oligonucleotide probes are used or when nucleic acids of high genetic complexity are analyzed, is that more than one complementary sequence may exist within the nucleic acid analyte for any given oligonucleotide probe, making it difficult to target the analysis to unique sites.

It is well known that in oligonucleotide hybridization, base mismatches at the terminal positions of the probe are difficult to discriminate against, while multiple mismatches are readily discriminated against and single internal mismatches are discriminated against to an intermediate extent and sometimes poorly. Furthermore, short oligonucleotide hybridization is known to be highly influenced by base composition, nearest neighbor and probe length, so that a large amount of experimentation is required in order to identify oligonucleotide probes that yield reliable and interpretable hybridization results, and furthermore, if an extensive oligonucleotide array is used, the numerous probes must be designed to form duplex structures (hybrids) of very similar thermal stability.

Stabilization of short duplex structures by base stacking interactions between tandemly hybridized (contiguously stacked) oligonucleotides has been described (Parinov et al, *Nucl. Acids Res.* 24:2998–3004, 1996; Yershov et al, *Proc. Natl. Acad. Sci., U.S.A.* 93:4913–4918, 1996; Khrapko et al, *FEBS Lett.* 256:118–122, 1989; Khrapko et al, *DNA Sequence* 1:375–388, 1991; Kieleczawa et al, *Science* 258:1787–1791, 1992; Kotler et al, *Proc. Natl. Acad. Sci., U.S.A.* 90:4241–4245, 1993; Kaczorowski & Szybalski, *Anal. Biochem.* 221:127–135, 1994; Kaczorowski & Szybalski, *Gene* 179:189–193, 1996; Lodhi & McCombie, *Genome Res.* 6:10–18, 1996; Johnson et al, *Anal. Biochem.* 241:228–237, 1996). Mutual stabilization of tandemly hybridized oligonucleotides was exploited in the use of a library of all 4096 hexamer primers to obtain readable dideoxy sequencing gels, wherein contiguous strings of three hexamers were annealed to the sequencing template, yielding a priming sequence of 18 bases with or without ligation (Kieleczawa et al, *Science* 258:1787–1791, 1992; Kotler et al, *Proc. Natl. Acad. Sci., U.S.A.* 90:4241–4245, 1993; Kaczorowski & Szybalski, *Anal. Biochem.* 221:127–135, 1994; Kaczorowski & Szybalski, *Gene* 179:189–193, 1996; Lodhi & McCombie, *Genome Res.* 6:10–18, 1996; Johnson et al, *Anal. Biochem.* 241:228–237, 1996). The Mirzabekov laboratory has shown that such contiguous stacking hybridization may be a viable strategy to resolve sequence ambiguities in sequencing by hybridization (Parinov et al, *Nucl. Acids Res.* 24:2998–3004, 1996; Khrapko et al, *FEBS Lett.* 256:118–122, 1989; Khrapko et al, *DNA Sequence* 1:375–388, 1991) and to identify specific point mutations (Yershov et al, *Proc. Natl. Acad. Sci., U.S.A.* 93:4913–4918, 1996). The contiguous stacking hybridization strategies taught by the Mirzabekov group, however, require multiple rounds of hybridization. Furthermore, these previous examples of stabilization of short oligonucleotide hybridization through contiguous stacking interactions were observed in hybridization reactions carried out in solution (Kieleczawa et al, *Science* 258:1787–1791, 1992; Kotler et al, *Proc. Natl. Acad. Sci., U.S.A.* 90:4241–4245, 1993; Kaczorowski & Szybalski, *Anal. Biochem.* 221:127–135, 1994; Kaczorowski & Szybalski, *Gene* 179:189–193, 1996; Lodhi & McCombie, *Genome Res.* 6:10–18, 1996; Johnson et al, *Anal. Biochem.* 241:228–237, 1996) or within a polyacrylamide gel matrix (Parinov et al, *Nucl. Acids Res.* 24:2998–3004, 1996; Yershov et al, *Proc. Natl. Acad. Sci., U.S.A.* 93:4913–4918, 1996; Khrapko et al, *FEBS Lett.* 256:118–122, 1989; Khrapko et al, *DNA Sequence* 1:375–388, 1991). The applicability of stacking hybridization has not been heretofore explored in the environment of a solid surface. Finally, the tandem or contiguous hybridization strategies of the prior art are applicable to analysis of nucleic acid sequences of limited genetic complexity, whereby primers or probes bind to a single unique site within the nucleic acid analyte. Thus, the tandem hybridization approaches of the prior art are inoperable in the analysis of extensive nucleic acid targets, such as complex mixtures of PCR fragments, expressed sequences or total genomes.

Due to deficiencies of the prior art there is a need for improved methods for analysis of numerous known mutations or DNA sequence polymorphisms, using short oligonucleotide probes immobilized on a solid surface. There is also a need for technologies that minimize the influence of probe length and sequence in short oligonucleotide hybridization analysis. There is furthermore a need for improved techniques for analysis of nucleic acid samples of high genetic complexity, using sequence-targeted oligonucleotide array hybridization. Also, there is a need for improved profiling of gene expression using numerous oligonucleotide probes targeted to mRNA species. Moreover, there is a need for more efficient identification of species, strains and individuals using DNA probe arrays designed to hybridize with numerous unique nucleotide sequences. There is in addition a need to adapt oligonucleotide array hybridization to directly analyze nucleic acid samples without the use of additional steps of target sequence amplification, single strand isolation and labeling. The present invention provides a simple, versatile strategy to overcome a variety of technical limitations associated with the prior art.

BRIEF DESCRIPTION OF THE DRAWINGS

FIG. 8 illustrates efficient mismatch discrimination at the end of a glass-tethered oligonucleotide probe using the tandem hybridization approach (contiguous stacking with labeled auxiliary oligonucleotide) of the disclosed invention.

FIG. 8A lists the sequences of the probes and labeled auxiliary oligonucleotide targets.

FIG. 9 shows the effect of hybridization temperature and washing duration on mismatch discrimination by stacking hybridization using an array of glass-tethered 9 mer probes. The results further illustrate that improved mismatch discrimination can be obtained at higher hybridization temperature and reveal that in the tandem hybridization method of the disclosed invention mismatch discrimination occurs primarily at the hybridization step rather than the washing step.

FIG. 12 shows the influence of mismatch position within the capture probe on mutation detection by tandem hybridization.

FIG. 12A is a listing the sequences, the mismatch type and the mismatch position of the capture probes.

FIG. 14 illustrates schematically the use of tandem hybridization to analyze short tandem repeat polymorphisms (STRPs) using allele-specific stacking probes (FIG. 14A) and allele-specific capture probes (FIG. 14B).

FIG. 15 illustrates in schematic form various embodiments of the disclosed invention using bead technology. In these approaches tandem hybridization is performed using capture probes tethered to color-coded polystyrene beads, which may be individually recognized and quantitated using flow cytometry and spectroscopic techniques.

SUMMARY OF THE INVENTION

Unlabeled nucleic acid analyte (the "target sequence") is denatured and annealed or hybridized with a molar excess of two or more oligonucleotide probes, at least one of which is labeled, and which bind to target sequences in one or more regions of known sequence, to form a partially duplex structure in which at least two oligonucleotide probes bind to the target sequence in tandem, forming a duplex region in which binding of at least one probe is stabilized by uninterrupted contiguous base stacking with the tandemly hybridizing probe. At least one of the oligonucleotides can be designed to disrupt interfering secondary or higher order structures, or to cover up alternative hybridization sites that any of the sequence-detecting probes may have within the nucleic acid analyte. This multiple probe strategy is designed to improve the reliability of hybridization analyses, and avoids the inconvenient and costly labeling of numerous nucleic acid samples. In addition, since the label is introduced only into specific target molecules that are targeted by the surface-tethered capture probes, the problem of nonspecific binding or imperfect hybridization is minimized, particularly with nucleic acid analytes of high genetic complexity. If different (distinguishable) labels are used in auxiliary oligonucleotides preannealed to different nucleic acid samples, a multiplicity of nucleic acid samples can be simultaneously analyzed in a single hybridization assay. If the nucleic acid target is a heat-denatured double-stranded DNA, the competing reassociation reaction of target strands can be minimized by preannealing the denatured target with a molar excess of oligonucleotides selected to bind to the target on one or both sides of the capture probe.

Figure 1:
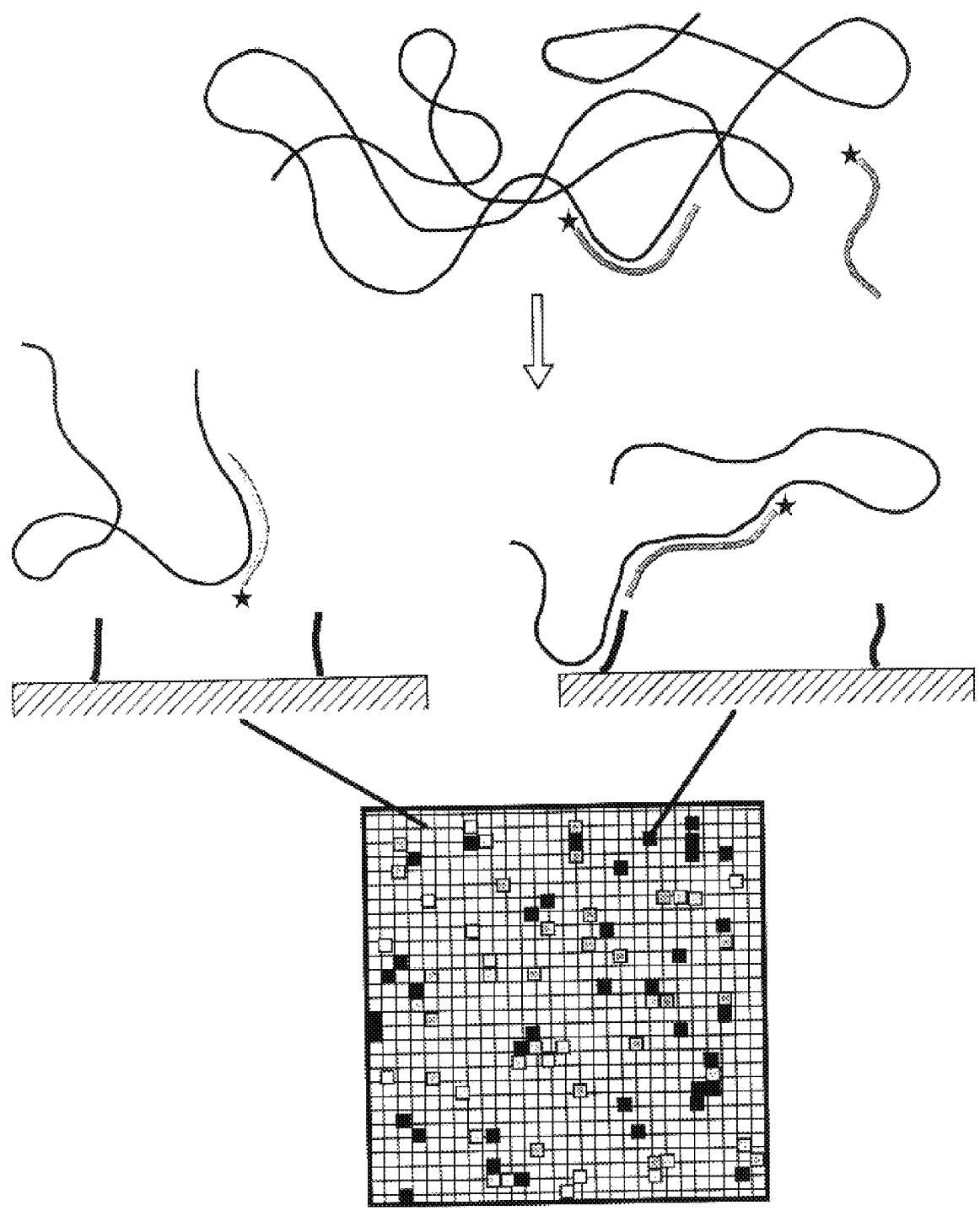
FIG. 1 depicts schematically the concept of the disclosed invention in a preferred embodiment of nucleic acid sequence analysis by tandem hybridization on sequence-targeted genosensor arrays.

In a typical embodiment of the disclosed invention, illustrated in FIG. 1, each labeled probe is designed to anneal to a unique site on the target strand, in tandem with a shorter surface-tethered "capture probe." Hybridization is carried out at elevated temperature or other increased stringency conditions, such that the short capture probe will not by itself form a stable duplex structure with the target sequence. Only if uninterrupted, contiguous base stacking occurs between labeled probe and surface-tethered capture probe, providing sufficient stability to the short duplex (capture probe paired with target strand), will a strong hybridization signal be seen. The labeled longer oligonucleotide is preferably preannealed to the target nucleic acid, however it can alternatively be added to the analyte nucleic acid at the time of hybridization to the array of surface-tethered capture probes. Increased site specificity is achieved because the analysis is targeted to a unique region on the nucleic acid analyte, complementary to the combined sequence of capture probe plus tandemly hybridizing labeled probe. Mismatches in the middle of the short capture probe or at any position extending to its junction with the tandemly hybridizing labeled probe will decrease the stability of the short duplex formed between target and capture probe, and will therefore reduce or eliminate the hybridization signal. Therefore, a collection of labeled "auxiliary" oligonucleotides, annealing on the target strand in tandem with a set of surface-tethered capture probes, arrayed at separate regions of a hybridization substrate, provides a robust means for simultaneous analysis of a multiplicity of nucleic acid sequences, and simultaneously, provides a convenient means for labeling of the analyte nucleic acid. An important feature of the disclosed invention is that since the longer labeled probes serve to position the hybridization of shorter capture probes to unique sites along the target, nucleic acids of high genetic complexity can be analyzed.

Thus, the use of auxiliary oligonucleotides, preannealed to the single-stranded target nucleic acid to form a partially duplex target molecule, offers several advantages in the analysis of nucleic acid sequences by hybridization to genosensor arrays or "DNA chips". These advantages include (i) a convenient means for introducing one or more labels into the target; (ii) prevention of short-range secondary structure that can interfere with hybridization to the surface-tethered oligonucleotide probes; (iii) masking of redundant sequences in the target strand to insure that a given capture probe interrogates a single site within the target; (iv) contiguous base stacking with the capture probe through tandem hybridization on the target strand, which enhances the hybridization signal and gives improved mismatch discrimination near the end of the capture probe; (v) ability to target the hybridization analysis to unique sites in nucleic acids of high genetic complexity; and (vi) improved ability to analyze double-stranded DNA targets by preannealing with a molar excess of oligonucleotides binding to the target adjacent to the capture probe.

The Mirzabekov laboratory previously described a contiguous stacking hybridization strategy for potential use in de novo sequencing by hybridization (Khrapko et al, *FEBS Lett.* 256:118–122, 1989; Khrapko et al, *DNA Sequence* 1:375–388, 1991), and recently reported the successful use of contiguous stacking hybridization to investigate point mutations (Yershov et al, *Proc. Natl. Acad. Sci., U.S.A.* 93:4913–4918, 1996). In the latter study the hybridization was carried out in two steps: The target DNA was first hybridized to decanucleotide probes (10 mers) covalently attached within a thin polyacrylamide gel matrix, to place the mutant site adjacent to the 10 mer duplex, then fluorescently labeled shorter contiguous stacking pentanucleotide probes (5 mers) were applied to the gel matrix to detect point mutations within the target sequence immediately adjacent to the 10-base duplex. In the invention disclosed herein, a related but distinct approach is used, wherein the shorter oligonucleotide probes are covalently attached in different positions on a solid surface, then the nucleic acid target, preannealed with one or more longer labeled oligonucleotides, each of which binds to the target in a unique position and may act as contiguous stacking oligonucleotides, is hybridized to the array.

Prior art indicates that when several hexamer oligonucleotides anneal in tandem on a single-stranded template DNA they form a contiguous sequence which acts efficiently as a primer for dideoxy DNA sequencing, with or without ligation (Kieleczawa et al, *Science* 258:1787–1791, 1992; Kotler et al, *Proc. Natl. Acad. Sci., U.S.A.* 90:4241–4245, 1993; Kaczorowski & Szybalski, *Anal. Biochem.* 221:127–135, 1994; Kaczorowski & Szybalski, *Gene* 179:189–193, 1996; Lodhi & McCombie, *Genome Res.* 6:10–18, 1996; Johnson et al, *Anal. Biochem.* 241:228–237, 1996). Studies of Lane et al. (*Nucl. Acids Res.* 25:611–616, 1997) indicated that base stacking energy between contiguous short oligonucleotides on the target DNA is responsible for increased hybrid stability. As disclosed herein, a similar stabilization effect occurs when a PCR fragment derived from the human cystic fibrosis gene is annealed with a stacking olignucleotide prior to hybridization with a surface-tethered probe, compared with hybridization without the "stacking" oligonucleotide. The Mirzabekov group proposed that the "stabilizing" effect of contiguous stacking can be used to improve the efficiency of de novo DNA sequencing by hybridization (Parinov et al, *Nucl. Acids Res.* 24:2998–3004, 1996) and to detect point mutations (Yershov et al, *Proc. Natl. Acad. Sci., U.S.A.* 93:4913–4918, 1996).

The Mirzabekov "contiguous stacking hybridization" (CSH) approach is designed to resolve sequence ambiguities remaining after a first hybridization on a complete sequencing by hybridization (SBH) array (Parinov et al, *Nucl. Acids Res.* 24:2998–3004, 1996; Drmanac et al, *Genomics* 4:114–128, 1989) or on a gene-targeted diagnostic array (Yershov et al, *Proc. Natl. Acad. Sci., U.S.A.* 93:4913–4918, 1996), by conducting one or more additional rounds of hybridization on the oligonucleotide array, using contiguously stacking probes. The tandem hybridization strategy disclosed herein is designed to detect known sequence variations, in a single hybridization reaction on the oligonucleotide array. Although the tandem hybridization approach disclosed herein has a more limited range of applications than Mirzabekov's CSH, it is much simpler, yet applicable to many important DNA diagnostic tests, where the relevant alleles are known from previous research. Furthermore, the auxiliary oligonucleotides annealed to the target nucleic acid in the hybridization strategy introduced here may serve to remove secondary structure from the target strand, such as interfering hairpin structures, and may also facilitate analysis of duplex target DNA. For example, prior to hybridization to an array of capture probes, a duplex DNA sample can simply be heat-denatured, then preannealed with a molar excess of auxiliary oligonucleotides, at least one serving as a contiguously stacking probe, the other annealing nearby to the DNA target on the other side of the capture probe, and one or both introducing the label, enabling detection of hybridization signal across the array of capture probes. Formation of these additional duplex regions flanking the test site should dominate over the competing reannealing reaction of complementary strands. Thus, the use of auxiliary oligonucleotide probes can eliminate two costly and time consuming steps that are normally conducted with each sample prior to hybridization, isolation of single-stranded target DNA and labeling of the target.

The CSH strategy used by the Mirzabekov laboratory to identify mutations (Yershov et al, *Proc. Natl. Acad. Sci., U.S.A.* 93:4913–4918, 1996) involved a first round of hybridization of a target DNA to an array of 10 mer probes immobilized within thin sections of polyacrylamide gel, followed by subsequent rounds of hybridization with fluorescent-labeled shorter (5 mer) probes, which hybridized to the target strand in tandem with the longer (10 mer) "capture probe." In the method disclosed herein a different approach is used, in which unlabeled target DNA is preannealed with a longer "stacking oligonucleotide," which also functions to introduce the label into the target molecule, then the partially duplex DNA target is hybridized with an array of shorter oligonucleotide probes tethered to a solid surface. One important distinction between the two approaches is that in Mirzabekov's CSH strategy the mismatch discrimination (nucleotide identification) occurs within the short stacking probe added in a subsequent round of hybridization on the oligonucleotide array, whereas in the method disclosed herein, the mismatch discrimination occurs within the short glass-tethered probe, in a single hybridization reaction on the oligonucleotide array. Thus, in the invention disclosed herein, sequence variations at each position of interest are represented within the short "capture probes" that are immobilized at separate locations on the surface, whereas in Mirzabekov's CSH approach, the sequence differences are represented in the short "stacking probes" added in subsequent rounds of hybridization. In the Mirzabekov approach the immobilized capture probes serve to position the target strand adjacent to the diagnostic fluorescent-labeled stacking probes added in one or more subsequent rounds of hybridization. In the tandem hybridization method disclosed herein it is the longer stacking oligonucleotide (annealed to the target) which serves to place the target strand in register with the shorter sequence-interrogating capture probe, and therefore the support-bound oligonucleotide and stacking oligonucleotides serve opposite roles in the two approaches.

The stacking hybridization method disclosed herein has several advantages over the more common oligonucleotide array approaches of the prior art, in which point mutations or single base polymorphisms are identified using immobilized allele-specific oligonucleotides (ASOs) without the stacking oligomer (Conner et al, *Proc. Natl. Acad. Sci., USA.* 80:278–282, 1983; Pease et al, *Proc. Natl. Acad. Sci., U.S.A.* 91:5022–5026, 1994; Hacia et al, *Nature Genetics* 14:441–447, 1996). In this more traditional method, a given nucleotide residue in the target is interrogated using probes differing at a single position in the middle of the oligomer sequence, and it is well known that in this system mismatch discrimination is efficient only in a central position of the probe. In the stacking hybridization strategy disclosed herein, however, mismatch discrimination is efficient at the terminal position of the immobilized oligonucleotide, adjacent to the stacking oligomer, as well as at internal positions within the surface-tethered capture probe. Thus, sequence changes can be detected over a greater stretch of sequence targeted by a given oligonucleotide probe using the stacking hybridization technique disclosed herein. In addition, since the strength of hybridization is increased by contiguous stacking interactions, greater hybridization occurs and therefore the detection sensitivity is effectively superior in the stacking hybridization approach. Mismatch discrimination may also be superior in the disclosed stacking hybridization approach, in the case of mismatches that are poorly discriminated in the center of a probe. These may be more disruptive when placed at the end of the capture probe, where base stacking with the contiguously hybridized oligomer will be disrupted.

A significant advantage of the stacking hybridization strategy disclosed herein over traditional ASO techniques is the ability to analyze sequences of high genetic complexity. An inherent disadvantage of standard ASO array methods for mutation detection is the need to use short oligonucleotide probes (7 mer–12 mer) in order to achieve good mismatch discrimination. For a probe of length, p, the average number of occurrences, n, of the probe within a target sequence of total length, L, is represented by the formula, $n=L/4^p$, and using this relationship, it is predicted that for an array of 8 mer probes, any given probe will have, on average, approximately 1.5 perfectly matched complements, in 100,000 bases of target sequence, and about 10% of 8 mers would occur more than once, on average, within a 10,000-base target sequence. Therefore, it would not be feasible to use 8 mer arrays in the standard ASO strategy for analyzing complex mixtures of fragments, such as a highly multiplexed PCR mixture. Similarly, it would not be feasible to use an array of 10 mers to directly analyze sequence variations within a complete bacterial genome or to analyze a complex mixture of expressed gene sequences from a higher eukaryotic organism, using traditional ASO hybridization methods. With the stacking hybridization approach of the disclosed invention, however, a labeled stacking oligonucleotide of greater length (eg. 15 mer), complementary to a unique site in a bacterial genome, is preannealed (at high stringency) with total bacterial DNA, such that upon hybridization with an array of short "capture probes," the labeled DNA binds specifically to an array element containing a short capture probe which hybridizes to the target strand in tandem with the labeled stacking oligonucleotide. In the disclosed invention, hybridization of analyte nucleic acid to the oligonucleotide array is carried out under conditions (eg., elevated temperature) in which the short surface-tethered capture probes do not form stable duplex structures with complementary sequences that may be present at distal locations within the target nucleic acid, not subject to stabilization by contiguous base stacking. Thus, the stacking hybridization approach enables direct analysis of target sequences of high genetic complexity. For genotyping applications, by providing a different long stacking probe for each "test site" on the target sequence, and by representing each allele (mutation or polymorphism) within the oligonucleotide array by a unique tandemly hybridizing capture probe, the disclosed tandem hybridization strategy enables analysis of numerous sequence variations within a target sequence of high genetic complexity. Similarly, the disclosed strategy may be used to quantitatively detect any expressed sequence in a bulk mRNA preparation. The applicability to nucleic acid analytes of high genetic complexity, combined with the use of the flowthrough chip configuration which enables analysis of dilute nucleic acid sequences (Beattie et al, *Clin. Chem.* 41:700–706, 1995; Doktycz & Beattie, In *Automated Technologies for Genome Characterization*, Beugelsdiik, Ed., J. Wiley & Sons, Inc., pp. 205–225, 1997; Beattie et al, In *Pharmacogenetics: Bridging the Gap Between Basic Science and Clinical Application, IBC Biomedical Library*, Schlegel, Ed., Southborough, Mass., pp. xx–yy, 1996), facilitates direct genotyping of complex genomes or analysis of expressed sequences, without PCR.

Although a preferred embodiment of the disclosed tandem hybridization invention is the use of short capture probes with long stacking probes, the invention also encompasses the use of short capture probes with short stacking probes, and the use of long capture probes with short or long stacking probes. For example, in the analysis of nucleic acids of high genetic complexity, an array of long surface-tethered oligonucleotides (each of length sufficient to hybridize with a single, unique sequence within the nucleic acid) may be used to first capture a unique sequence at each array element (such as a specific mRNA species, a DNA fragment derived from a specific gene transcript by reverse transcription, or a specific genomic region), then one or more labeled stacking probes may be hybridized to the array to reveal the relative abundance of target sequences bound to each array element (such as a transcriptional profile) or to reveal the allele status of a collection of polymorphic markers. The labeled stacking probes and arrayed capture probes may alternatively be hybridized to the nucleic acid sample in a single step.

The disclosed invention additionally includes the use of DNA ligase to covalently join the surface-tethered capture probe to the labeled stacking probe following hybridization to the oligonucleotide array. This ligation step preferentially stabilizes the hybridization signal that arises from contiguous stacking between capture and stacking probes, while having no effect on label bound to the array through any other means, including nonspecific hybridization and isolated hybridization of capture and labeled probes to different (noncontiguous) sites on the target strand. The ligation approach is particularly advantageous when nucleic acids of high genetic complexity are analyzed using short capture probes. Following ligation, a washing step can be carried out at elevated temperature, to remove absolutely all label except that that which has bound to the array via contiguous stacking hybridization. Furthermore, since the ligation reaction is well known to be inhibited by base mismatches at the ligation junction, the strategy of ligation followed by washing at elevated temperature can improve the discrimination against mismatched bases at or adjacent to the termini of capture and stacking probe in the disclosed tandem hybridization approach. Consequently, the combined tandem hybridization/ligation strategy can improve the identification of mutations and DNA sequence polymorphisms. The ligation approach can be applied in a variety of embodiments using different numbers and lengths of capture and stacking probes, including the use of multiple stacking probes flanking (on one or both sides) the capture probe; the use of short capture probes with either short or long stacking probes; and the use of long capture probes with either short or long stacking probes. For each pair of tandemly hybridizing oligonucleotides to be joined by ligation, one must bear a 3'-hydroxyl and the other a 5'-phosphate. The 5'-phosphate group can be incorporated in a variety of ways well known to the practioner, including chemical phosphorylation during the chemical synthesis of oligonucleotides using the standard phosphoramidite procedure, and phosphorylation of oligonucleotides using polynucleotide kinase. In the latter case, the kinase reaction can be applied to free oligonucleotides in solution, or can be carried out "in situ" with oligonucleotides immobilized at their 3'-ends on a solid surface.

An important feature inherent to the disclosed invention, which is particularly advantageous for analysis of nucleic acids of high genetic complexity, is that specific sequences are captured at each array element, in other words, each hybridization site (or array element) serves to purify a specific sequence among a complex mixture of sequences. Whether the unique sequence capture occurs as the end result of stacking hybridization with or without ligation, or whether it occurs in the initial hybridization of the nucleic acid to an array of long surface-tethered capture probes, the purified sequences are available for further analytical steps, which can include one or more additional hybridization steps on the array substrate, or elution of the bound (purified) sequences from one or more array elements, for further analysis or manipulation (including sequencing, cloning, and additional hybridization reactions). The quantity of sequence captured at each array element and the elution/recovery of bound material may be optimized through the use of a flowthrough hybridization substrate comprised of any high surface area support material, including but not limited to glass fiber filters, micromachined or etched silicon structures, microchannel glass, porous plastics, arrays of encapsulated microbeads, etc.

DETAILED DESCRIPTION OF THE INVENTION

To facilitate a detailed understanding of the present invention the following definitions of terms and acronyms are provided.

Hybridization—in the field of nucleic acid analysis, a term originally used to denote the formation of a duplex structure between complementary strands of RNA and DNA ("RNA/DNA hybrid"), but currently used widely to include any duplex formation between complementary strands, whether DNA/DNA, DNA/RNA, or RNA/RNA, carried out either in solution or in the solid phase, wherein one of the two strands is immobilized onto a solid surface or matrix.

Annealing—in the field of nucleic acid analysis, a term originally used to describe the process of duplex formation in which two nucleic acids are mixed together, heated to denature the duplex structure, then incubated at slowly decreasing temperature to allow complementary sequences to find themselves and form new duplex structures, accommodating a range of base compositions and strand lengths. The term is used more recently (including herein) to mean incubation of a single-stranded or heat-denatured duplex nucleic acid analyte with an oligonucleotide probe or primer, under hybridization conditions enabling the probe or primer to bind to its complementary sequence within the analyte nucleic acid, either at slowly decreasing temperature or at a single temperature.

Analyte or analyte nucleic acid—the class of compound in a sample which is the object of analysis, for example a nucleic acid extracted from a biological sample.

Label (also known as "tag")—a substituent that can be attached to a nucleic acid analyte which enables its detection land or quantitation. Examples include radiolabels such as $^{32}P$, $^{33}P$ and $^{35}S$; fluorescent tags, chemiluminescent tags, enzymes that catalyze formation of a fluorescent, chemiluminescent or colored compound, ligands such as biotin, and chemical groups that are distinguishable by mass or other spectroscopic properties. The label may be introduced into the analyte nucleic acid by a variety of means, including chemical reaction, incorporation of labeled nucleotide by enzymatic reaction (including polymerase, kinase or ligase), or by hybridization or annealing of a labeled probe with the analyte nucleic acid.

Probe—a nucleic acid sequence used as a reagent to bind its complementary sequence within the analyte nucleic acid, via a hybridization reaction.

Sequence—a string of bases within a nucleic acid, comprising A, G, C, T residues in DNA or A, G, C, U residues in RNA, linked together in a specific order and chain length. A sequence can contain any or all of the four bases.

Complementary or complementary sequence—two sequences are said to be complementary if they are capable of forming a two-stranded (duplex) structure in which all of the bases in one strand form specific Watson-Crick base pairs (A•T or G•C in DNA; A•U and G•C in RNA) with the opposing bases in the opposite strand. The term can also be used at the single base pair level: A is complementary to T or U; T or U are complementary to A; G is complementary to C; C is complementary to G.

Noncomplementary or noncomplementary sequence—two sequences are said to be noncomplementary if they do not form a perfectly Watson-Crick base-paired duplex structure. Imperfectly base paired duplex structures sometimes form (though usually less stable than a perfectly paired duplex) in which a small fraction of the opposing bases are noncomplementary (A opposite G, C; G opposite A, T or G; C opposite T, A or C; or T opposite G, C or T).

Labeled probe—as used herein, an oligonucleotide bearing one or more detectable labels or tags, which is capable of binding to its complementary sequence within a nucleic acid analyte, enabling the detection and/or quantitation of said analyte nucleic acid.

Capture probe—as used herein, an oligonucleotide of specific sequence bound at one end (tethered) to a solid surface, enabling the capture of a nucleic acid analyte containing a complementary sequence onto said solid surface, in a hybridization reaction.

Stacking probe—as used herein, an oligonucleotide designed to bind to its complementary sequence within a nucleic acid analyte, immediately adjacent to (in tandem with) the complementary sequence within the nucleic acid analyte which hybridizes with a capture probe. The stacking probe and capture probe hybridize in tandem with the target strand to form a duplex region of length equal to the sum of the lengths of stacking and capture probes, in which all of the bases in one strand are Watson-Crick base-paired with opposing bases on the opposite strand. At the junction between stacking and capture probes there is uninterrupted base stacking interaction between the terminal residues of stacking and capture probes. The stacking probe is normally labeled and is normally of length sufficient to have a single, unique binding site (complementary sequence) within the nucleic acid analyte. The base stacking interactions propagating from the stacking probe into the capture probe results in stabilization of the binding of target strand to the surface-tethered capture probe, yielding an effective duplex stability similar to that which would be obtained using a (longer) capture probe of length equal to the combined lengths of capture and stacking probes. The stacking probe is normally designed to be of length sufficient to possess a single, unique complementary sequence within the analyte nucleic acid.

Partially duplex structure—a nucleic acid molecule that is partially single-stranded and partially duplex, such as the structure formed upon annealing of an oligonucleotide with a longer single-stranded nucleic acid strand.

Target, target sequence, target strand or target nucleic acid—a nucleic acid sequence whose presence in the analyte is the object of detection, for example (as used herein), through hybridization with a specific DNA probe. The term, "target nucleic acid" refers to a specific molecule, strand or fragment (such as a single mRNA species or a specific PCR fragment) that is the object of detection, for example via hybridization to a labeled DNA probe. The term "target sequence" is sometimes used in a broad sense to mean the nucleic acid molecule or fragment bound by a DNA probe, or can be used in a restricted sense to mean the specific nucleotide sequence within the target nucleic acid which binds to the DNA probe via complementary base pairing.

Unique position within the target nucleic acid—as used herein, an oligonucleotide probe (typically, a labeled stacking probe) is said to bind (or hybridize) to a unique position within the target nucleic acid when the oligonucleotide is of length sufficient to have only a single complementary sequence within the analyte nucleic acid, thus is capable of binding at a single, unique position within the analyte nucleic acid.

Tethered, or Surface-tethered—as used herein, a DNA probe (typically an oligonucleotide) is said to be surface-tethered or tethered to a surface if it is bound at one end with the surface, through a covalent bond or otherwise strong bond formed between a functional group on the surface and a functional group at one end of the DNA probe.

Base stacking—the major force accounting for the stability of duplex nucleic acid structures, comprising electronic interactions between adjacent planar bases within each strand. Base stacking is normally an intrastrand force which propagates along a strand and is much stronger when two strands are Watson-Crick base paired in a duplex structure. The longer the duplex region, the stronger the stabilizing stacking interactions within each strand, which largely accounts for the well known length dependence of duplex stability.

Contiguous stacking—as used herein, base stacking interactions propagating through the junction of two oligonucleotides hybridizing in tandem with a target nucleic acid; the stacking probe and the capture probe are contiguously stacked when hybridized in tandem on the target strand, to form a combined length of duplex equal to the sum of the lengths of stacking and capture probes.

Tandem hybridization—as used herein, a hybridization reaction carried out using a surface-tethered oligonucleotide (the "capture probe") and an auxiliary oligonucleotide (the "stacking probe," which is typically labeled and preannealed with the target), wherein the capture probe and stacking probe bind at adjacent (non-overlapping but contiguous) sites on the target strand, forming a contiguous duplex structure in which stacking and capture probes interact with one another through base stacking interactions.

Solid phase hybridization—a hybridization reaction conducted in which one of the two "reactant strands" participating in formation of a duplex structure is immobilized on a solid support.

Auxiliary oligonucleotide—as used herein, an oligonucleotide which performs an "auxiliary" function in a solid phase hybridization assay, different from that of the surface-tethered capture probe. Said auxiliary functions include labeling of the analyte nucleic acid (performed by the labeled probe); stabilization of the duplex formed between target strand and capture probe (performed by the stacking probe); and enabling the binding of the capture probe to a single, unique position within the target nucleic acid (also performed by the stacking probe).

Flanking—adjacent to each other along a sequence.

Mutation—any heritable change in nucleotide sequence within a genome, occurring spontaneously or induced by chemical damage to DNA.

DNA sequence polymporphism—naturally occurring variation in the DNA sequence within a population of a given species, generally considered useful as DNA markers if the frequency of a minor allele is greater than about 10% in the population.

Oligonucleotide—short nucleic acid (DNA or RNA) strand, which can be chemically synthesized, typically of length up to about 100 nucleotides.

Gene—a unit of genetic function, including sequences encoding a protein or functional RNA (eg., rRNA or tRNA), intronic (noncoding) sequences interpersed within a gene, and additional sequences functioning in the regulation of the gene.

Genome—the entire complement of genes, intergenic sequences and other genetic elements that comprise an organism or autonomously replicating entity.

Amplicon—a fragment of DNA amplified using the polymerase chain reaction.

Genotype—A collection of detectable DNA sequence variations (polymorphisms or markers) that may distinguish one individual from another; also a verb meaning the act of determining a genotype.

Transcription—formation of RNA species (individual mRNA, rRNA and tRNA "transcripts") from individual genes, typically catalyzed by RNA polymerase. In vivo transcription occurs to yield a wide range of abundancies of individual gene transcripts, from none to many millions of copies per cell, depending on cell type and physiological state.

Gene expression—the process of biosynthesis of gene products from genes of an organism, including the processes of transcription, intron splicing (in eukaryotes), translation of mRNA into protein, and posttranslational modification of proteins to give altered activity or function.

Multiplex—in the field of nucleic acid analysis, refers to the ability to detect a mixture of simultaneously occurring reactions or entities, such as formation and detection of multiple PCR products in a single reaction, and detection of multiple nucleic acids in a mixture, through use of distinguishable tags or through spatial separation into distinct sites.

DNA chip or genosensor chip—a two-dimensional array of surface-tethered DNA probes formed on a surface, enabling simultaneous analysis of a multiplicity of hybridization reactions. The "chip" (also termed "microarray") is typically in a miniaturized format, with individual DNA probes arrayed at center-to-center spacing of one millimeter or less.

Secondary structure—any double-stranded structure formed between two complementary or largely complementary sequences. The term includes interstrand duplex formation, such as in annealing and hybridization reactions, as well as intrastrand duplex formation, such as hairpin loops.

Hairpin loop or stem-loop—a type of intrastrand secondary structure formed when two inverted repeat sequences occur near each other (eg., AGCCTGtatCAGGCT)—the inverted repeat sequences (denoted here by capital letters) fold back on each other to form a duplex region (hairpin stem) and the short sequence between the inverted repeats (denoted here by lower case letters) forms the single-stranded loop at the top of the stem. Intrastrand formation of stable hairpin loops within a target nucleic acid can interfere with the availability of the target sequence to hybridize with a surface-tethered oligonucleotide that is complementary to a sequence within the hairpin-loop.

Mismatch—the existence of one or more base mispairings (or "noncomplementary base oppositions") within a stretch of otherwise complementary duplex-forming (or potentially duplex-forming) sequences. The existence of a single mismatched base pair within a short oligonucleotide duplex (termed a "mismatched hybrid") normally destabilizes the duplex.

Mismatch discrimination—as used herein, the ability of a surface-tethered oligonucleotide probe to hybridize specifically to a fully complementary sequence, and not to a mismatch-containing (nearly complementary) sequence.

Reverse transcriptase—a DNA polymerizing enzyme which polymerizes deoxynucleoside triphosphates to form a complementary DNA ("cDNA") strand using an RNA template strand hybridized with an appropriate primer strand (which is elongated during the "reverse transcription").

Primer—a nucleic acid sequence (such as an oligonucleotide) possessing a free 3'-OH terminus, which is base paired with a "template strand" and thus can be elongated by a polymerase enzyme. For example, an oligonucleotide primer annealed with a DNA template can serve as a substrate (along with deoxynucleoside 5'-triphosphates) for a DNA polymerase, resulting in "primer extension," as in the PCR reaction.

Genetic complexity—the total length of nonrepetitive, unique sequence within a nucleic acid analyte. An example of high genetic complexity is an entire genome and an example of low genetic complexity is a single PCR fragment.

Thermal stability—The stability of a duplex nucleic acid structure as a function of temperature in a given salt/buffer solution. It is well known that thermal stability increases with increased length of a nucleic acid duplex. It is also well known that thermal stability of s short duplex region (formed by hybridization of an oligonucleotide probe with a single-stranded target) can be substantially increased by contiguous base stacking with a tandemly hybridized oligonucleotide. For example, the thermal stability of two tandemly hybridized 7 mer oligonucleotides (contiguously stacked on a complementary strand) is similar to that of a single 14 mer hybridized to its complement.

PCR fragment—a fragment of DNA of defined length (defined by the spacing between priming sites on the template) formed by the polymerase chain reaction Expressed sequence—an RNA molecule formed by transcription of a coding sequence(s) within a gene (typically mRNA but also including rRNA, tRNA), or alternatively, a complementary DNA (cDNA) copy of the RNA, formed by an in vitro reverse transcription reaction.

Denature (denatured)—separation (dissociation) of the two strands of a duplex nucleic acid molecule under conditions which destabilize the double helix, most commonly, elevation of temperature ("heat-denaturation").

Preanneal—as used herein, the annealing (or hybridization) of a heat-denatured analyte nucleic acid with one or more auxiliary oligonucleotides prior to hybridization of the analyte to surface-tethered capture probes.

Allele—a specific member of a collection of naturally occurring sequence variants (detectable within a population of individuals) at a specific genomic locus or marker.

Homozygous—in a diploid genome, the occurrence of an identical allele on both copies of the relevant chromosome.

Heterozygos—in a diploid genome, the occurrence of different alleles on the two copies of the relevant chromosome.

DNA marker—a defined genomic site containing naturally occurring DNA sequence variation (detectable within a population of individuals) which can be analyzed using biochemical techniques to determine the allele status, including homozygous/heterozygous state and any other properties related to the sequence variation (such as length of restriction fragment or PCR fragment, or sequence identity as revealed by hybridization analysis or DNA sequencing).

Redundant residue—a position within a sequence (for example, an oligonucleotide) which is occupied by a mixture of two or more (and typically all four) bases.

Repetitive sequence—a sequence that exists in numerous copies within a genome, for example SINE (including Alu) sequences in the human genome and short tandem repeat sequences (including ACACACACAC . . . ) scattered throughout the genomes of higher eukaryotes.

5'-end/terminus—the end of a nucleic acid chain containing a nucleotide with a non-esterified carbon-5 on its deoxyribose (or ribose).

3'-end/terminus—the end of a nucleic acid chain containing a nucleotide with a non-esterified carbon-3 on its deoxyribose (or ribose).

PCR—polymerase chain reaction
PNA—peptide nucleic acid
SBH—sequencing by hybridization
CCD—charge coupled device
LCR—ligase chain reaction
ASO—allele-specific oligonucleotide
SNP—single nucleotide polymorphism
STRP—short tandem repeat polymorphism
SINE—short interspersed repetitive element present in hundreds of thousands of copies scattered across a higher eukaryotic genome. The most extensively studied mammalian SINE is the Alu sequences, comprising a 282 consensus sequence, typically followed by an A-rich region and flanked by direct repeat sequence representing the duplicated insertion site. Alus are repeated on average, every 3,000 base pairs in the human genome.

LINE—long interspersed repetitive element

SSC—standard saline citrate, a solution containing 150 mM sodium chloride and 15 mM sodium citrate TMAC—tetramethyl ammonium chloride The auxiliary oligonucleotide annealing/tandem hybridization strategy of the disclosed invention offers improved performance in many important oligonucleotide hybridization applications, including: (i) repetitive analysis of known mutations or sequence polymorphisms in numerous genomic samples; (ii) simultaneous analysis of numerous known mutations or sequence polymorphisms in single genes, a multiplicity of genes, or on a genome-wide scale; (iii) identification of species, strains or individuals through the use of oligonucleotide probes and auxiliary oligonucleotides targeted to nucleotide sequences known to be unique for said species, strains or individuals; (iv) analysis of gene expression (transcription) profiles through the use of oligonucleotide probes and auxiliary oligonucleotides known to be unique to individual mRNA species; and (v) analysis of nucleic acid samples of high genetic complexity. Furthermore, the strategy of labeling the target strands by annealing with labeled auxiliary oligonucleotides can increase the convenience and cost effectiveness of high throughput nucleic acid sequence analyses, and the labeling can be done with a number of nonradioactive tags, using reagents that generate fluorescence, chemiluminescence or visible colors in the detection step.

The following examples are given for the purpose of illustrating various embodiments of the invention and are not meant to limit the present invention in any fashion.

EXAMPLE 1

Preparation of Arrays of 5'-tethered Oligonucleotide Probes and Formation of Labeled Partially Duplex Target DNA Molecules A Microlab 2200 robotic fluid-delivery system (Hamilton, Reno, Nev.), supplied with a four-needle delivery head, was used to place submicroliter droplets onto glass slides. The Microlab 2200 system was programmed (using resident software) to deliver droplets of 200 nL onto each slide as previously described (Beattie et al, *Molec. Biotechnol.* 4:213–225, 1995; Beattie et al, *Clin. Chem.* 41:700–706, 1995).

Oligonucleotides were synthesized at Genosys Biotechnologies (The Woodlands, Tex.) by means of the standard phosphoramidite procedure (49) and an efficient multiple synthesis strategy (Beattie & Frost, U.S. Pat. No. 5,175,209, 1992; Beattie et al, *Appl. Biochem. Biotechnol.* 10:510–521, 1988; Beattie & Hurst, In *Innovation and Perspectives in Solid Phase Synthesis, Proc. 3rd International Symposium on Solid Phase Synthesis*, Epton, Ed., Mayflower Worldwide Ltd., Birmingham, U.K., pp. 69–76, 1994). Phosphoramidites for introduction of 5'-amino linker into oligonucleotides were obtained from Glen Research (Sterling, Va.).

Glass microscope slides were epoxysilanized for probe attachment as previously described (Beattie et al, *Molec. Biotechnol.* 4:213–225, 1995; Beattie et al, *Clin. Chem.* 41:700–706, 1995). Oligonucleotide probes containing 5'-terminal amino modification were dissolved in $H_2O$ to a final concentration of 20 μM, and 200 nL droplets of each probe were applied to the epoxysilanized glass slides using a Hamilton Microlab 2200 station equipped with a multi-probe head. Rows of three droplets of each probe were attached to observe the reproducibility of the results. Before hybridization the slides were soaked for 1 hr at room temperature with blocking agent (10 mM tripolyphosphate) and then rinsed with water and air dried.

Genomic DNA was isolated from peripheral blood leukocytes from normal individuals and from cystic fibrosis (CF) patients. Mutation ΔF508 was originally tested by Southern analysis. The haplotypes of allele ΔF508 in the DNA samples were confirmed by the mobility of the products formed by the polymerase chain reaction (PCR) in 10.5% polyacrilamide gel electrophoresis. For this purpose a pair of PCR primers, CF163 (5'-GCACAGTGGAAGAATTTCATTCTG (SEQ ID NO: 2)) and CF164 (5'-ACCTCTTCTAGTTGGCATGCTTTG (SEQ ID NO: 3)), was used to amplify a 138-bp fragment derived from exon 10 in the CFTR gene. This fragment contains four of the most frequent sites of mutations causing cystic fibrosis, Q493X, ΔI507, ΔF508 and V520F (Tsui, *Trends Genet.* 8:392–398, 1992).

To prepare natural single-stranded target DNA by PCR, primer CF164 labeled with biotin at the 5' end, was used. The PCR product was processed with a Millipore (Bedford, Mass.) Ultrafree spin-filter (30,000 $M_r$ cutoff) to remove the excess of PCR primers, and the material retained was applied in two portions to AffiniTip™ Strep 20 columns (Genosys Biotechnologies). The single-stranded DNA fragment was eluted with 20 μL of 0.2 N NaOH per column, and the solution was neutralized with 4 μl of 1N HCl.

To form partially duplex, labeled target DNA molecules, $^{32}P$-labeled auxiliary oligonucleotides (CF164, CF168, CF169 and CF170) were preannealed to the single-stranded PCR fragment, as follows. Five pmol of oligonucleotide CF164 or CF170 was labeled by kinasing with an excess of $\gamma^{32}P$-ATP (23 mM, specific activity 7000 Ci/mmol). Aliquots of single-stranded target DNA were annealed either with CF164, with all the auxiliary oligonucleotides, or with all the auxiliary oligonucleotides except CF164. The annealing mixture contained 50 μl 20×SSC, 10 μl 1M Tris-HCl (pH 8.0), 3 μl 0.5M EDTA, one or more prelabeled auxiliary oligonucleotide (0.23 pmol each), 10 μl single-stranded target DNA, and HPLC-pure $H_2O$ to 90 μl. The mixture was incubated at 95° C. for 5 min, 45° C. for 5 min, then 6° C. 5 min. Excess $\gamma^{32}P$-ATP was removed by microcentrifugation through an Ultrafree spin-filter (30,000 $M_r$ cutoff), and the retained DNA was dissolved in 20 μL of 1×SSC.

Auxiliary oligonucleotides designed to produce partially duplex structure across the target sequence included CF164 (sequence listed above), CF168 (5'-ATGAAATTCTTCCACTGTGC (SEQ ID NO: 4)), CF169 (5'-TTCTTTAATGGTGCCAGGCATAATCCAGGA (SEQ ID NO: 5)), and CF170 (5'-GTATCTATATTCATCATAGGAA (SEQ ID NO: 6)). These oligonucleotides anneal to the single-stranded 138-base PCR product derived from exon 10 of the human CFTR gene (see below).

Each of four possible CF mutations in the 138-b target was represented on the slide by a pair of probes, one complementary to the wild type allele and the other complementary to the mutant allele. Each probe was derivatized to carry a primary amino group at the 5'-terminus, which covalently bound to the epoxysilanized glass. The sequences of the eight 9-mer probes were as follows (the 5'-amino group is denoted by the character, "@". For mutation Q493X, probes CF10W 5'-@actgagaac (SEQ ID NO: 7) and CF10M 5'-@taagaacag (SEQ ID NO: 8); for mutation ΔI507, probes CF11W 5'-@aagatgata (SEQ ID NO: 9) and CF11M 5'-@ccaaagata (SEQ ID NO: 10; for mutation ΔF508, probes CF12W 5'-@ccaaagatg (SEQ ID NO: 11) and CF12M 5'-@caccgatga (SEQ ID NO: 12); and for mutation V520F, probes CF13W 5'-@atgacgctt (SEQ ID NO: 13) and CF13M 5'-@gatgaagct (SEQ ID NO: 14).

The alignment of the glass-tethered probes and auxiliary oligonucleotides with the 138-base normal target strand is shown below.

```
<---------CF163-------->                                                    (SEQ ID NO: 1)

GCACAGTGGAAGAATTTCATTCTGTTCTCAGTTTTCCTGGATTATGCCTGGCACCATTAAAGAAAATATCATCTTTGGTGT cgtgtcaccttcttaaagta          aggacctaataccgaccgtggtaatttctt (CF168)    (CF10W)caagagtca@       (CF169)     (CF11W)atagtagaa@

(CF10M)gacaaga_a@                   (CF11M)_atagaaacc@

(CF12W)gtagaaacc@

(CF12M)ag_ta_gccac@

TTCCTATGATGAATATAGATACAGAAGCGTCATCAAAGCATGCCAAGTAGAAGAGGT aaggatactacttatatctatg         gtttcgtacggttgatcttctcca (CF170)    (CF13W)ttcgcagta@       (CF164)

(CF13M)tcg_aagta_g@
```

The normal target sequence is shown in capital letters, with positions of mutations underlined. The "forward primer" (CF163) is indicated at the 5'-end. Aligned below the target sequence are the auxiliary oligonucleotides and the glass-tethered probes with 5'-amine denoted by "@." The subscript letters in the probe sequences correspond to positions of mismatch with the normal target.

Figure 2:
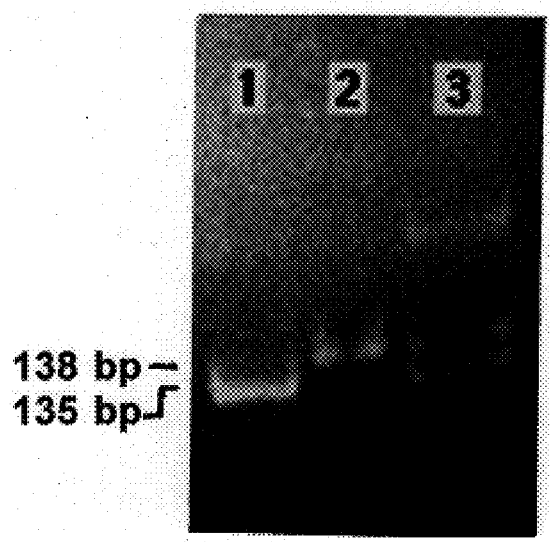
FIG. 2 displays the electrophoretic analysis of the ΔF508 mutation, a 3-base deletion in the human CFTR gene. The results show the distinct electrophoretic banding patterns formed by PCR fragments bearing wild-type, homozygous mutant, and heterozygous (wild-type/mutant) allelic status at the ΔF508 mutational site.

To verify the haplotypes of human donors (normal, homozygous ΔF508 and heterozygous wt/ΔF508), DNA samples were subjected to PCR amplification using primers CF163 and CF164 and the products were analyzed by electrophoresis in 10.5% polyacrylamide gels. As shown in FIG. 2, the DNA sample with homozygous ΔF508 mutation yielded a PCR product (lane 1) of greater mobility than the normal DNA (lane 2). The heterozygous DNA sample yielded both bands plus a third band with lower mobility (lane 3). When the third band was isolated and reamplified with the same primers, the electrophoretic gel showed again the same three bands. In addition, the third band was positively amplified with nested primers, suggesting that the third band corresponds to a hybrid duplex DNA fragment formed by one strand of normal sequence paired with a ΔF508 strand (data not shown).

Figure 3:
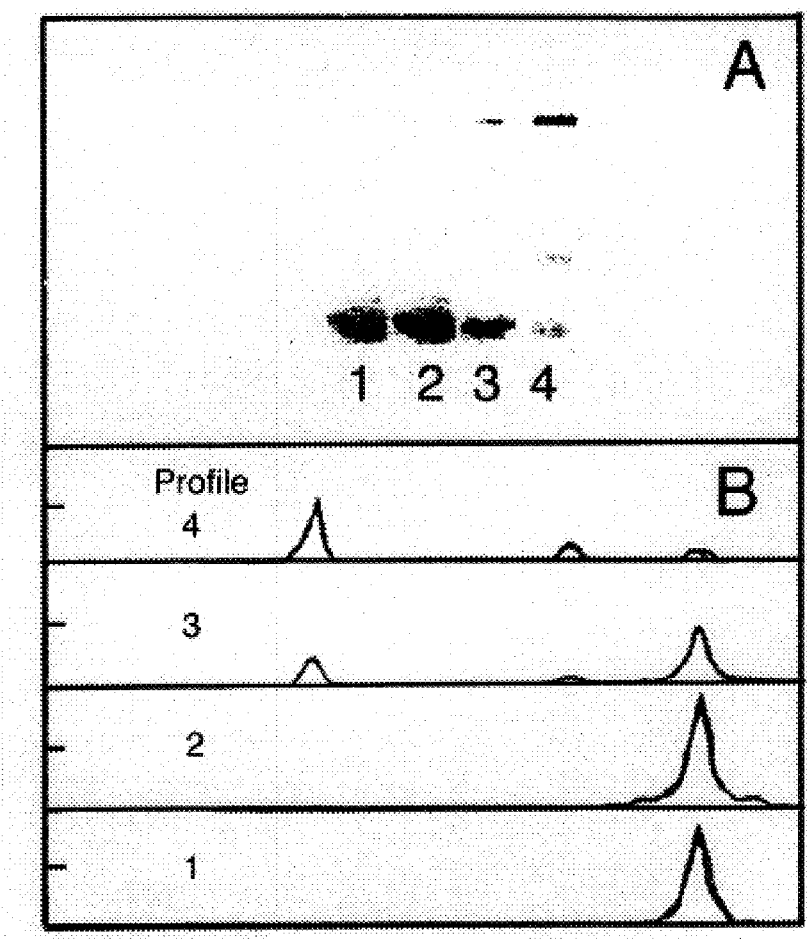
FIG. 3 characterizes the annealing of auxiliary oligonucleotide CF164 with single-stranded target DNA, showing the quantity of auxiliary oligonucleotide required to form a duplex structure with a given quantity of target strand prior to hybridization to the oligonucleotide array.

To establish that the single-stranded target DNA has been annealed to the auxiliary oligonucleotides and to determine the amount of target strand needed to completely bind a given quantity of $^{32}$P-labeled auxiliary oligonucleotide, a series of annealing reactions were performed, varying the proportion of target DNA at a fixed amount of auxiliary oligonucleotide. Aliquots of 0, 1, 2 and 5 µL of target DNA, prepared as described above, were annealed to 1 µL (0.5 pmol) of labeled CF164 primer and the products were analyzed by gel electrophoresis under nondenaturing conditions. The autoradiogram and its profile of band intensities are shown in FIG. 3. As expected, the intensity of the upper band, corresponding to the labeled auxiliary oligonucleotide bound to target DNA, increased with increasing quantity of target strand, while the lower band, corresponding to the free oligonucleotide, decreased. Curiously, a minor band was seen (visible in lane 4) with electrophoretic mobility intermediate between that of CF164 and the target fragment. This band also increased with higher target concentration, suggesting that the target fragment contained a minor proportion of shorter PCR product, possibly due to primer dimer formation or alternative priming within the target. Nevertheless, this analysis reveals the quantity of target DNA needed to incorporate the labeled auxiliary oligonucleotide into the partially duplex form, prior to hybridization to the oligonucleotide probe array.

EXAMPLE 2

Hybridization of CF Target DNA to Glass-tethered Probes, Using One or More Labeled Auxiliary Oligonucleotides Array hybridization of labeled target molecules (prepared as described in Example 1) to oligonucleotide arrays tethered to glass slides (prepared as described in Example 1) was carried out in 3.3M tetramethylammonium chloride (TMAC) dissolved in 50 mM Tris-HCl (pH 8.0), 2 mM EDTA, 0.1% (w/v) Na dodecyl sulfate and 10% (w/v) polyethylene glycol (Beattie et al, *Molec. Biotechnol.* 4:213–225, 1995; Beattie et al, *Clin. Chem.* 41:700–706, 1995). A 20-µL aliquot of labeled target DNA or target DNA annealed with one auxiliary oligonucleotide (labeled-CF164), three auxiliary oligonucleotides (CF168, CF169 and labeled CF170), or all four auxiliary oligonucleotides (CF164, CF168, CF169 and labeled CF170), was placed onto each slide and a cover slip was applied. Slides were incubated in a humid environment, such as a water bath, overnight at 15° C. or 25° C. After hybridization the slides were washed by dipping several times in the corresponding hybridization solution without PEG, air dried, then wrapped in plastic film and placed against X-ray film for autoradiography.

Figure 4:
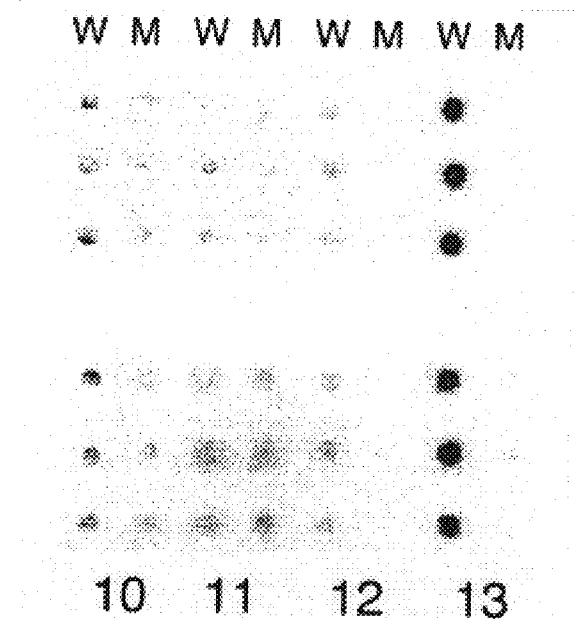
FIG. 4 shows a hybridization pattern which indicates the feasibility of using the strategy of preannealing an unlabeled target strand with labeled auxiliary oligonucleotides, in mutation analysis by oligonucleotide array hybridization.

To validate the preannealing/labeling strategy using one or more auxiliary oligonucleotides, for mutation analysis by oligonucleotide array hybridization, the normal target DNA (preannealed with labeled CF164 or with all four auxiliary oligonucleotides) was hybridized to glass slides containing a variety of 9 mer probes representing normal and mutant sequences in the CF target (displayed in Example 1). The eight glass-tethered probes, placed in triplicate on the slides, represented perfect matches plus a variety of mismatches with the normal (wild-type) target sequence, at both internal and terminal positions along the probes. The hybridization patterns are shown in FIG. 4. In the case of target preannealed with labeled CF164 (FIG. 4, Panel A), hybridization dots were clearly observed with the wild-type probes (CF10W, CF11W, CF12W and CF13W). Probe CF13W yielded a much more intense hybridization signal than the other probes, presumably due to stacking interactions with auxiliary oligonucleotide CF164, which hybridizes contiguously (in tandem) with CF13W on the target strand. Hybridization signal intensities with the mutant probes varied from essentially undetectable for CF12M and CF13M to barely lower than for the corresponding wild-type probes (CF10M and CF11M), which is consistant with previous reports that mismatch discrimination depends on the type, location and number of mismatches between target and probe (Maskos & Southern, *Nucl. Acids Res.* 20:1675–1678, 1992; Mirzabekov, *Trends Biotechnol.* 12:27–32, 1994; Khrapko et al, *FEBS Lett.* 256:118–122, 1989; Khrapko et al, *DNA Sequence* 1:375–388, 1991; Meier-Ewert et al, *Nature* 361:375–376, 1993). Inspection of the sequences (listed in Example 1) reveals that the mutant probes that yielded hybridization signals nearly as intense as their wild-type counterparts (CF10M and CF11M) produce a single mismatch with the normal target sequence, at a terminal position along the probe. Mutant probe CF12M, which yielded nearly undetectable hybridization with the normal target labeled with CF164 (FIG. 4, Panel A), produces two internal mismatches with the target, whereas mutant probe CF13M, which gave a barely detectable hybridization signal, produces one internal mismatch with the target, plus one overlapping base with tandemly hybridized CF164. The hybridization patterns obtained with target preannealed with all four auxiliary oligonucleotides (CF164 and CF170 labeled; CF168 and CF169 unlabeled) showed a similar pattern of hybridization (FIG. 3, Panel B), except that the hybridization signals were slightly more intense, as expected. The results shown in FIG. 4 indicate the feasibility of using the strategy of preannealing an unlabeled target strand with labeled auxiliary oligonucleotides, in mutation analysis by oligonucleotide array hybridization.

Figure 5:
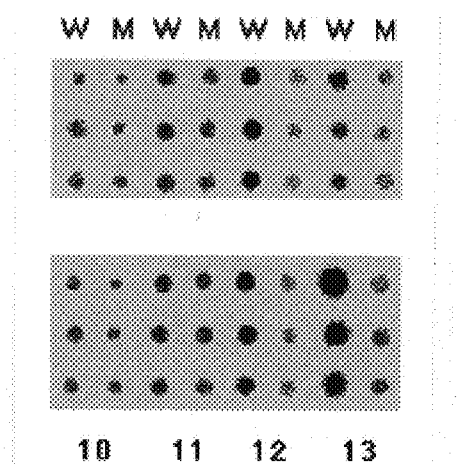
FIG. 5 displays the hybridization of wild-type target DNA, preannealed with different auxiliary oligonucleotides, to an array of glass-tethered 9 mer probes. The results show that contiguous base stacking between a 9 mer capture probe and a longer labeled auxiliary oligonucleotide yields a strong hybridization signal and enables efficient discrimination between wild-type and mutant target sequences.

An experiment was performed to confirm the hypothesis that the intense hybridization of probe CF13M to the target (relative to the other probes) was due to stacking interactions with auxiliary oligonucleotide CF164. This experiment was identical to that of FIG. 4, except that preannealing to the target was carried out in the presence and absence of auxiliary oligonucleotide CF164, and the results are shown in FIG. 5. When the target was preannealed with all four auxiliary oligonucleotides the pattern of hybridization (FIG. 5, Panel B) was essentially identical to that obtained in the previous experiment (FIG. 4). In the absence of oligonucleotide CF164, however, a much lower hybridization intensity with probe CFW13 was obtained (FIG. 5, Panel A), which was now similar to that obtained with the other probes. Therefore, the great enhancement of hybridization signal for probe CF13W was likely due to stacking interactions with the tandemly hybridized auxiliary oligonucleotide CF164. Notably, the single internal mismatch between probe CF13M and the normal target was poorly discriminated against (similar hybridization intensity as the corresponding wild-type probe) in the absence of the tandemly hybridizing auxiliary oligonucleotide.

EXAMPLE 3

Discrimination of ΔF508 Mutation in Homozygous and Heterozygous Samples

Figure 6:
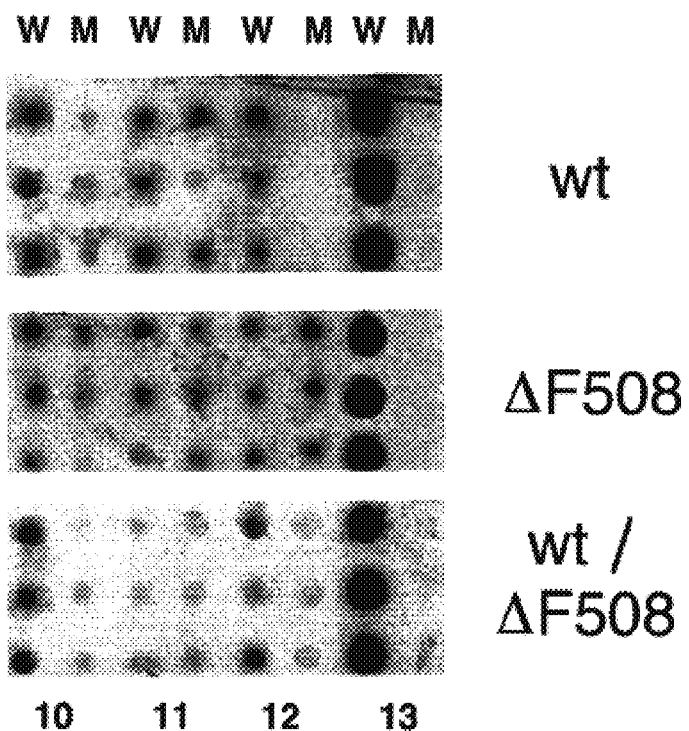
FIG. 6 displays the hybridization of partially duplex wild-type, homozygous ΔF508 and heterozygous wild-type/ΔF508 target DNA, preannealed with auxiliary oligonucleotides, to an array of 9 mer probes tethered to glass. The results show that normal (wild-type), homozygous mutant, and heterozygous allelic states can be distinguished using the disclosed invention of tandem hybridization on genosensor arrays.

To assess whether normal (wild-type), homozygous ΔF508 mutant, and heterozygous wt/ΔF508 DNA samples (see FIG. 2) can be discriminated using the auxiliary oligonucleotide/tandem hybridization strategy disclosed herein, the single-stranded PCR products derived from these samples were preannealed with the four auxiliary oligonucleotides, then hybridized at 15° C. for 4 hr with slides containing the set of eight 9 mer probes. The results are displayed in FIG. 6. As expected, the hybridization patterns for probes interrogating other mutant sites (CF 10, 11 and 13) were similar to those seen in FIGS. 4 and 5. Similarly, the hybridization of probes CF12W and CF12M with the wild-type target showed good signal with the wild-type probe and little or no signal with the mutant probe, as in the previous experiments. However, with the homozygous ΔF508 mutant target, the mutant probe (CF12M) gave slightly stronger hybridization than the wild-type probe (CF12W), which produces one internal mismatch and one terminal mismatch with the normal target. This hybridization intensity of the "mutant" probe (CF12M) with homyzygous mutant target would probably have been even stronger, except that a mistake in the design of the sequence of CF12M was made, under the incorrect assumption that the ΔF508 mutation is due to deletion of TTT (actually it is due to deletion of CTT). Thus, there is still a single internal mismatch between probe CF12M and the mutant target sequence. Nevertheless, when the DNA prepared from heterozygous wt/ΔF508 mutant sample was analyzed by oligonucleotide array hybridization, the hybridization pattern (with the pair of probes, CF12W and CF12M) was intermediate between the patterns produced by wild-type and homozygous mutant samples. Thus, the hybridization strategy disclosed herein can be used to discriminate between homozygous and heterozygous condition at the ΔF508 site.

EXAMPLE 4

Influence of Hybridization Temperature

Figure 7:
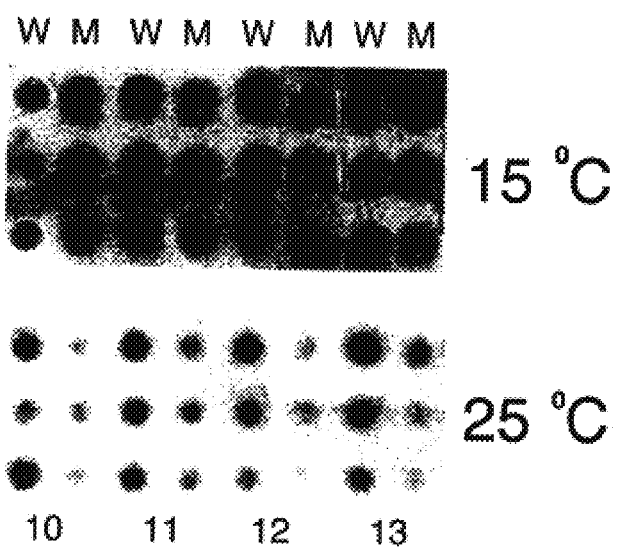
FIG. 7 depicts the effect of hybridization temperature on mutation detection by hybridization of target DNA (preannealed with labeled auxiliary oligonucleotide) to an array of glass-tethered 9 mer probes. The results further illustrate the utility of introducing a label into the target strand by preannealing with labeled oligonucleotide and indicate that superior mismatch discrimination using 9 mer probes is achieved at 25° C. hybridization temperature compared with 15° C.

The analysis of the heterozygous wt/ΔF508 sample using the 8-probe array was repeated, using this time a preannealing mixture lacking CF164, and using two different temperatures (15° C. and 25° C.) during hybridization of the target to the array of glass-tethered probes. The results are shown in FIG. 7, with the time of exposure to the X-ray film chosen to obtain good signal at 25° C. As in FIG. 5, Panel A, there was rather poor mismatch discrimination using hybridization at 15° C. When the hybridization was conducted at higher temperature (25° C.), however, the mismatch discrimination was clearly improved.

EXAMPLE 5

Hybridization of Synthetic Target Molecules to 3'-tethered Oligonucleotide Arrays Placement of oligonucleotide probe droplets onto glass slides was carried out manually, or with the aid of a Microlab 2200 fluid delivery robot (Hamilton, Reno, Nev.), as described previously (Beattie et al, *Molec. Biotechnol.* 4:213–225, 1995; Beattie et al, *Clin. Chem.* 41:700–706, 1995). Quantitation of $^{32}$P-labeled target molecules bound across the hybridization array was carried out by autoradiography, followed by scanning of the X-ray films using a flat bed scanner.

$\gamma^{32}$P-ATP (7,000 Ci/mmol, 100 μCi/μL) was obtained from ICN Radiochemicals (Irving, Calif.). Microcon 3 filters were acquired from Amicon (Beverly, Mass.). The oligonucleotides were synthesized at Genosys Biotechnologies (The Woodlands, Tex.) by means of the standard phosphoramidite procedure (Matteucci & Caruthers, *J. Am. Chem. Soc.* 103:3185–91, 1981), using a parallel synthesis strategy (Beattie & Frost, U.S. Pat. No. 5,175,209, 1992; Beattie et al, *Appl. Biochem. Biotechnol.* 10:510–521, 1988; Beattie & Hurst, In *Innovation and Perspectives in Solid Phase Synthesis, Proc. 3rd International Symposium on Solid Phase Synthesis*, Epton, Ed., Mayflower Worldwide Ltd., Birmingham, U.K., pp. 69–76, 1994). Introduction of 3'-aminopropanol linker into oligonucleotide probes was accomplished by use of C3-Aminolink CPG (Glen Research, Sterling, Va.) during the synthesis. The names, sequences and roles of the oligonucleotides used are:

| Name | Sequence (5'- > 3') | Role |
| --- | --- | --- |
| CF164 | 5'- CCTCTTCTAGTTGGCATGCTTTG (SEQ ID NO: 3) | stacking oligonumer |
| CFW13 | 5'- ATGACGCTT@ (SEQ ID NO: 15) | probe |
| CF195 | 5'- TTGACGCTT@ (SEQ ID NO: 16) | probe |
| CF196 | 5'- CTGACGCTT@ (SEQ ID NO: 17) | probe |
| CF197 | 5'- GTGACGCTT@ (SEQ ID NO: 18) | probe |
| CFW13-P | 5'-PATGACGCTT@ (SEQ ID NO: 19) | probe |
| CF195-P | 5'-PTTGACGCTT@ (SEQ ID NO: 20) | probe |
| CF196-P | 5'-PCTGACGCTT@ (SEQ ID NO: 21) | probe |
| CF197-P | 5'-PGTGACGCTT@ (SEQ ID NO: 22) | probe |
| CFW13-8 | 5'- ATGACGCT@ (SEQ ID NO: 23) | probe |
| CF195-8 | 5'- TTGACGCT@ (SEQ ID NO: 24) | probe |
| CF196-8 | 5'- CTGACGCT@ (SEQ ID NO: 25) | probe |
| CF197-8 | 5'- GTGACGCT@ (SEQ ID NO: 26) | probe |
| CFW13-7 | 5'- ATGACGC@ (SEQ ID NO: 27) | probe |
| CF195-7 | 5'- TTGACGC@ (SEQ ID NO: 28) | probe |
| CF196-7 | 5'- CTGACGC@ (SEQ ID NO: 29) | probe |
| CF197-7 | 5'- GTGACGC@ (SEQ ID NO: 30) | probe |
| CFW13-6 | 5'- ATGACG@ (SEQ ID NO: 31) | probe |
| CF195-6 | 5'- TTGACG@ (SEQ ID NO: 32) | probe |
| CF196-6 | 5'- CTGACG@ (SEQ ID NO: 33) | probe |
| CF197-6 | 5'- GTGACG@ (SEQ ID NO: 34) | probe |
| CF179 | 5'- AGAAGCTTCATCAAAGCAT GCCAACTAGAAGAGG (SEQ ID NO: 35) | synthetic target |
| CF180 | 5'- AGAAGCTTCAGCAAAGCAT GCCAACTAGAAGAGG (SEQ ID NO: 36) | synthetic target |
| CF181 | 5'- AGAAGCTTCACCAAAGCAT GCCAACTAGAAGAGG (SEQ ID NO: 37) | synthetic target |
| CF182 | 5'- AGAAGCTTCAACAAAGCAT GCCAACTAGAAGAGG (SEQ ID NO: 38) | synthetic target |
| CF179-7G | 5'- AGAAGCGTCATCAAAGCAT GCCAACTAGAAGAGG (SEQ ID NO: 39) | synthetic target |
| CF180-7G | 5'- AGAAGCGTCAGCAAAGCAT GCCAACTAGAAGAGG (SEQ ID NO: 40) | synthetic target |
| CF181-7G | 5'- AGAAGCGTCACCAAAGCAT GCCAACTAGAAGAGG (SEQ ID NO: 41) | synthetic target |
| CF182-7G | 5'- AGAAGCGTCAACAAAGCAT GCCAACTAGAAGAGG (SEQ ID NO: 42) | synthetic target |

The "@" at the 3'-end of probes denotes the amino modification used for attachment to glass slides. The "P" at the 5'-end of some probes denotes phosphorylation.

An improved procedure for tethering oligonucleotides to underivatized glass surfaces (Doktycz & Beattie, In *Automated Technologies for Genome Characterization*, Beugelsdiik, Ed., J. Wiley & Sons, Inc., pp. 205–225, 1997; Beattie et al, In *Pharmacogenetics: Bridging the Gap Between Basic Science and Clinical Application*, IBC Biomedical Library, Schlegel, Ed., Southborough, Mass., pp. xx–yy, 1996; Beattie, In *DNA Markers: Protocols, Applications and Overviews*, Caetano-Anolles & Gresshoff, Eds., J. Wiley & Sons, 1997) was used. Glass microscope slides were prepared for probe attachment by soaking in hexane and absolute ethanol for 20 min. each, then dried for 5 hr at 80° C. Oligonucleotide probes containing 3'-terminal aminopropanol modification were dissolved to a final concentration of 20 $\mu$M in $H_2O$, and 200-nL droplets of each probe were applied by hand or using a Hamilton Microlab 2200 fluid dispensing robot, to the hexane/ethanol-washed glass slides. Two rows of three droplets of each probe, distributed as described above, were attached to increase the reliability of the results. Before hybridization the slides were soaked for 1 hr at room temperature with a blocking solution comprised of 10 mM tripolyphosphate, and then rinsed with water and air dried.

To prepare labeled, partially duplex target molecules containing the "stacking" oligonucleotide contiguous to the binding site of the glass-tethered "capture probes," the following procedure was used. Twenty pmol of "stacking" oligonucleotide CF164 was labeled by incubation with 1 $\mu$L of $\gamma^{32}$P-ATP (23 $\mu$M, 7000 Ci/mmol), 1 $\mu$L (10 U) T4 polynucleotide kinase, 3 $\mu$L 10×kinase buffer, and sterile water to 30 $\mu$L final volume. After 1 hr at 37° C. the reaction was stopped with 3 $\mu$L of 0.5M EDTA. Aliquots of 8 $\mu$L were annealed with 5 pmol of each synthetic target (CF179, CF180, CF181 and CF182) in the following annealing mixture: 50 $\mu$L 20×SSC; 10 $\mu$L 1M Tris-HCl, pH 8.0; 3 $\mu$L 0.5M EDTA; 7.5 $\mu$L labeled "stacking" oligonucleotide; 1 $\mu$L synthetic target; and $H_2O$ to 100 $\mu$L. The annealing mixture was incubated at 95° C. for 5 min; at 45° C. for 5 min; then at 6° C. for 5 min. The excess radioactive ATP and other substances were removed by centrifugation through microcon 3 until the volume was approximately 20 $\mu$L, followed by, two more cycles of addition of 200 $\mu$L SSC and centrifugation down to 20 $\mu$L volume.

Hybridizations to oligonucleotide probes arrayed on glass slides were performed in 3.3M tetramethylammonium chloride (TMAC) plus 50 mM Tris-HCl (pH 8.0), 2 mM EDTA, 0.1% (w/v) sodium dodecyl sulfate, 10% (w/v) polyethylene glycol, plus 20 $\mu$L (5 pmol) of the partially duplex target strand. Hybridization was carried out for 3 hr at 25° C. or at the temperature indicated, under saturated humidity conditions (within a water bath). After hybridization the slides were washed for 5 min by dipping into fresh hybridization buffer without PEG. Slides were air dried, wrapped in plastic film, and placed against X-ray film for autoradiography. Autoradiograms were converted to digital image using a flat bed scanner.

EXAMPLE 6

Mismatch Discrimination by Stacking Hybridization

Figure 8A:
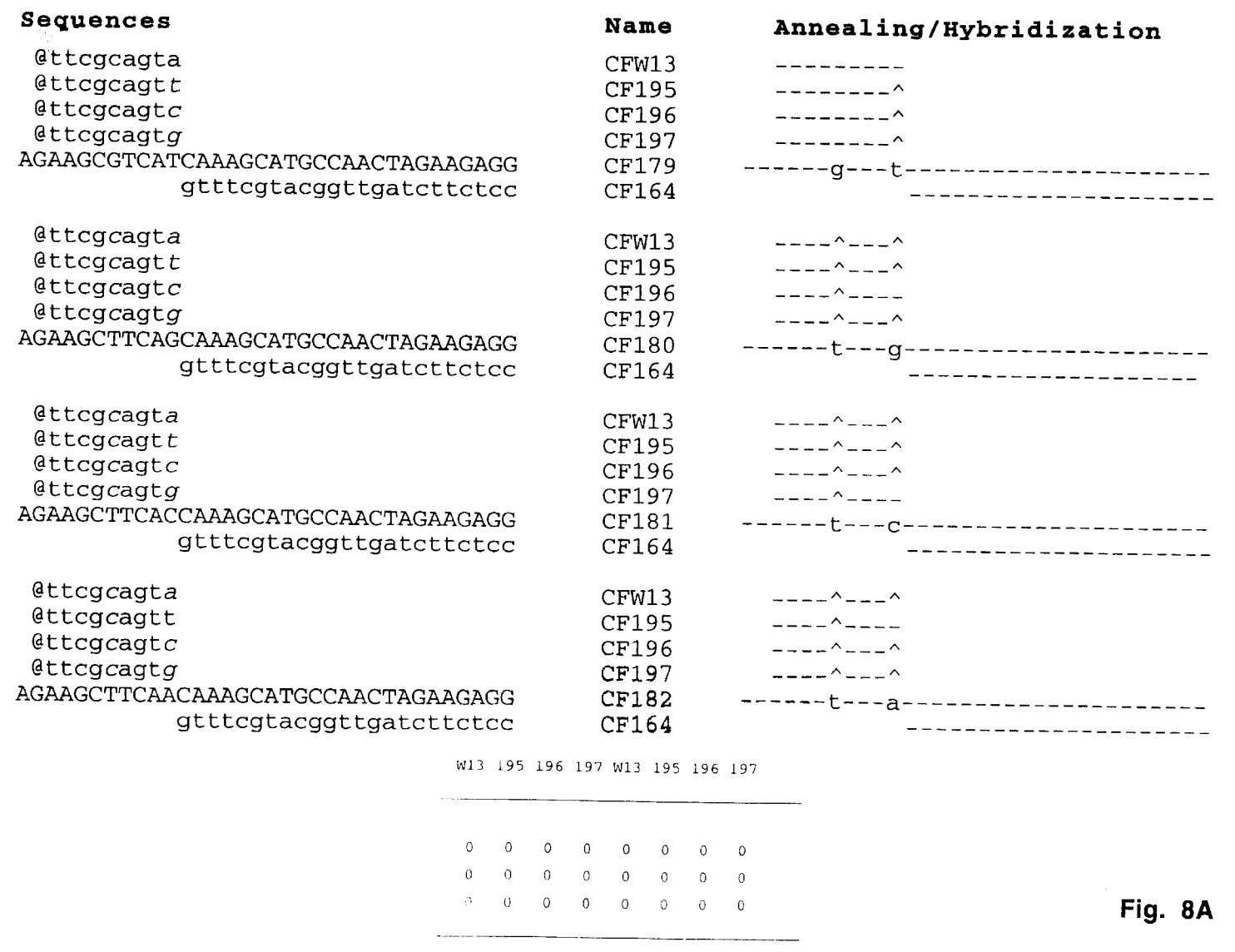
Figure 8B:
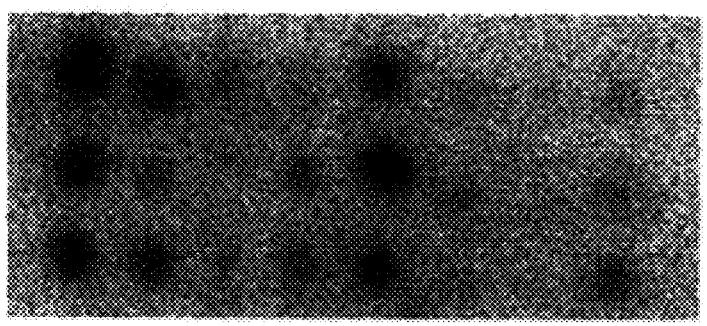
FIG. 8B shows the results of the tandem hybridization approach to achieve efficient mismatch discrimination.
Figure 8B:
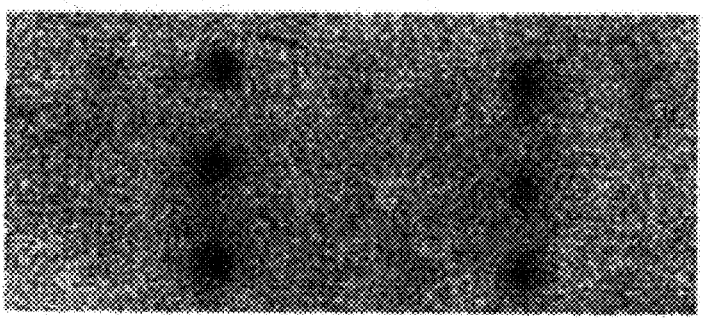
Figure 8B:
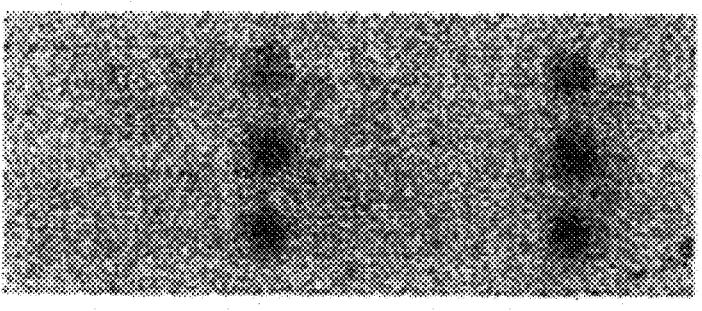
Figure 8B:
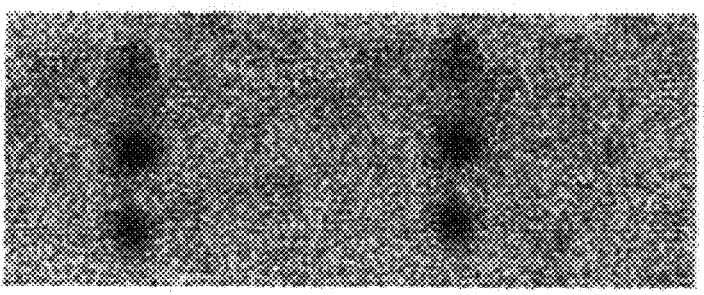

The discrimination of mismatches at the 5'-termini of glass-tethered 9 mer probes, hybridized at 25° C. to synthetic target strands containing contiguously stacked ($^{32}$P-labeled) CF164, was assessed using the 16 basic combinations of probes (W13, 195, 196, 197) and synthetic targets (CF179, CF180, CF181, CF182) preannealed with labeled stacking oligonucletide CF164 as described in Example 5. The results are shown in FIG. 8. The sequences of targets and probes are displayed in FIG. 8A and hybridization results are shown in FIG. 8B. With synthetic target CF179 the strongest hybridization signal was obtained with the perfectly matched probe (CFW13), a lower signal was seen with probes 195 and 197 (producing T•T and G•T terminal mismatches, respectively), and there was barely detectable hybridization with probe 196 (producing a C•T terminal mismatch). Lower hybridization intensities were observed with targets CF180, CF181 and CF182, which produced an internal C•T mispair with the probes, in addition to having the variable residue opposite the 5'-terminal mismatch position on the probes. Interestingly, the destabilizing effect of the internal mismatch created very high mismatch discrimination at the 5'-terminus of the glass-tethered probes, adjacent to the stacking oligomer. At 25° C. significant hybridization occurred only with the 9 mer probes containing a perfect match at the junction with the stacking oligonucleotide. This phenomenon could be useful in design of capture probes for optimal mismatch discrimination using the stacking oligonucleotide strategy.

EXAMPLE 7

Influence of Hybridization Temperature and Washing Time

Figure 9A:
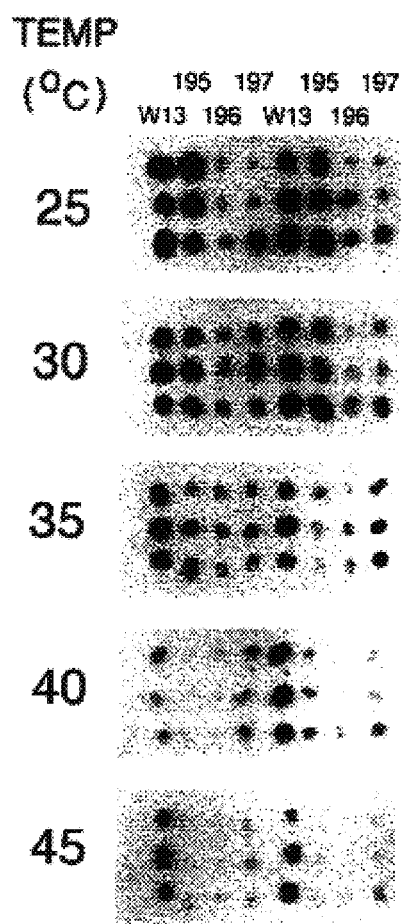
In FIG. 9A shows the hybridization dots after 3 hr hybridization at each temperature, followed by 5 min washing at the same temperature.
Figure 9B:
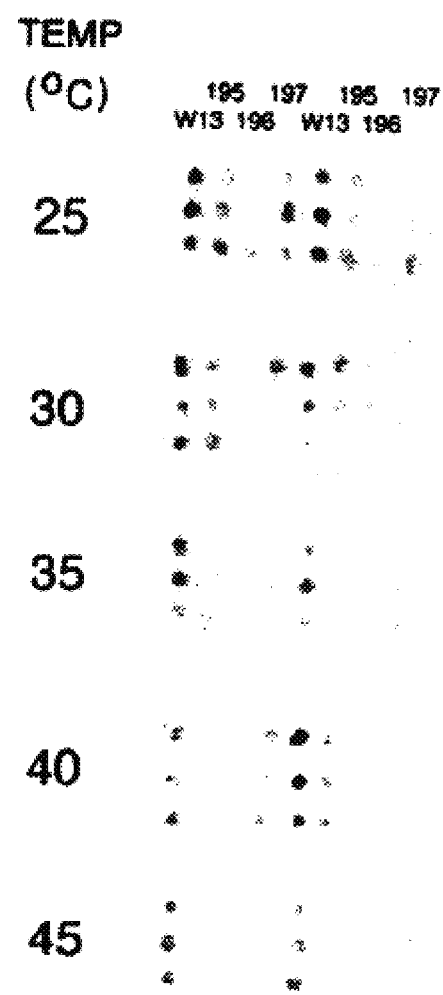
FIG. 9B shows the results after continued washing for successive 1-hr periods at 30, 35, 40 and ending with 45° C.

In Example 4 it was shown that terminal mismatch discrimination using 9 mer capture probes with the stacking oligomer preannealed to single-stranded PCR product was better when hybridization was carried out at 25° C. than at 15° C. An experiment was carried out to test whether further improvement of the mismatch discrimination with the 9 mer probes can be obtained at yet higher hybridization and washing temperatures. The experiment of FIG. 8 (using target CF179) was repeated at 25, 30, 35, 40 and 45° C. and the results are shown in FIGS. 9A and 9B. In FIG. 9A are shown the hybridization dots after 3 hr hybridization at each temperature, followed by 5 min washing at the same temperature. The hybridization signal decreased with increasing temperature, while simultaneously, the mismatch discrimination increased and was very good at 45° C. FIG. 9B shows the results after continued washing for successive 1-hr periods at 30, 35, 40 and ending with 45° C. Because very little change was observed when the slides were washed at the lower temperatures (data not shown), only the results after the final 45° C. washing are shown. The major effect of extensive washing at the higher temperature was decreased hybridization signal; mismatch discrimination, as reflected by the relative intensity of different signals, was only minimally improved by extended washing. Apparently, in the stacking (tandem) hybridization system mismatch discrimination occurs primarily at the binding step (forward reaction), rather than during washing (dissociation reaction).

EXAMPLE 8

Influence of Probe Length and Phosphorylation

Figure 10:
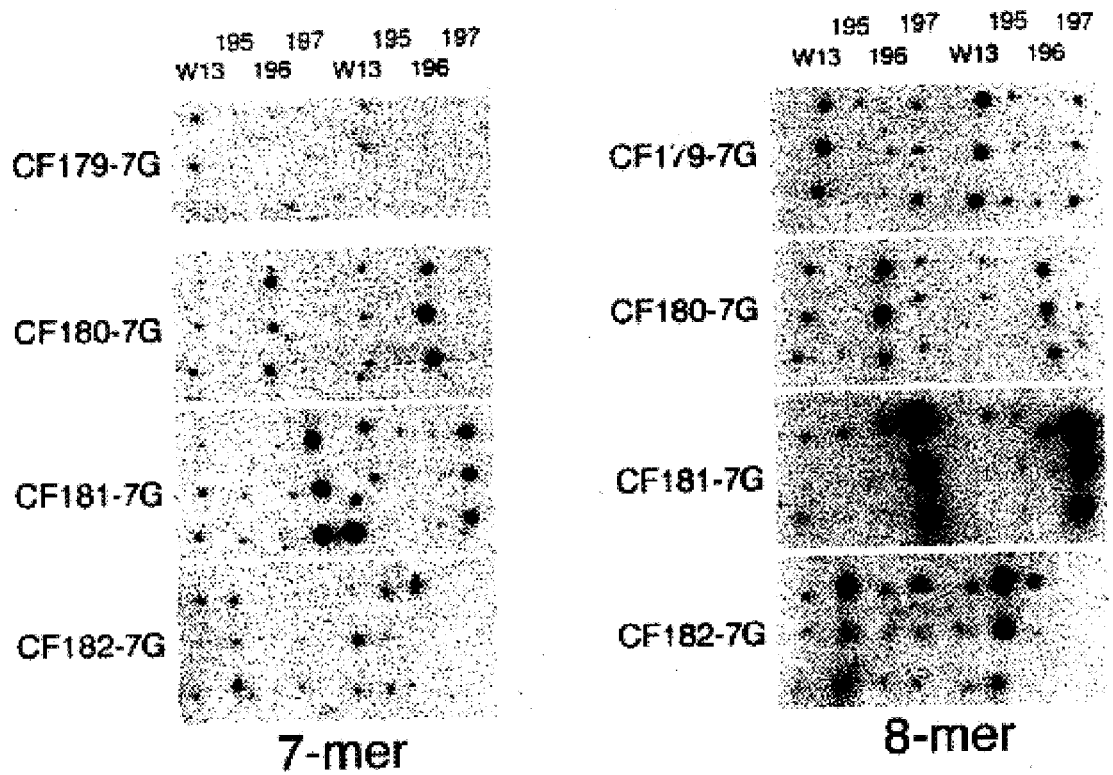
FIG. 10 illustrates the influence of the length of glass-tethered capture probe (7 mer versus 8 mer here, in comparison with 9 mer data of FIG. 8) on mismatch discrimination by tandem hybridization performed at 25° C. The results indicate that improved mismatch discrimination at the end of the capture probe can be achieved using shorter capture probes in the disclosed invention.

Experiments were performed to assess the influence of probe length and 5'-phosphorylation of the probe on mismatch discrimination by tandem hybridization at 25° C. FIG. 10 shows the results of an experiment similar to that of FIG. 8 (Example 6), except that the probe length was 8 mer and 7 mer (rather than 9 mer) and the synthetic targets contained no internal mismatch with the probe. Comparison of the upper image in FIG. 10 with the upper image in FIG. 8 gives a reasonable indication of the effect of probe length (9 mer, 8 mer, 7 mer) at the 25° C. hybridization temperature. As the probe length decreased there was decreased hybridization signal but increased mismatch discrimination at the 5'-end of the probe, adjacent to the stacking oligonucleotide. In hybridizations of synthetic templates 180-7G, 181-7G and 182-7G with the 7 mer and 8 mer probes there was likewise good mismatch discrimination, with the strongest hybridization occurring with the perfectly matched probe.

Figure 11:
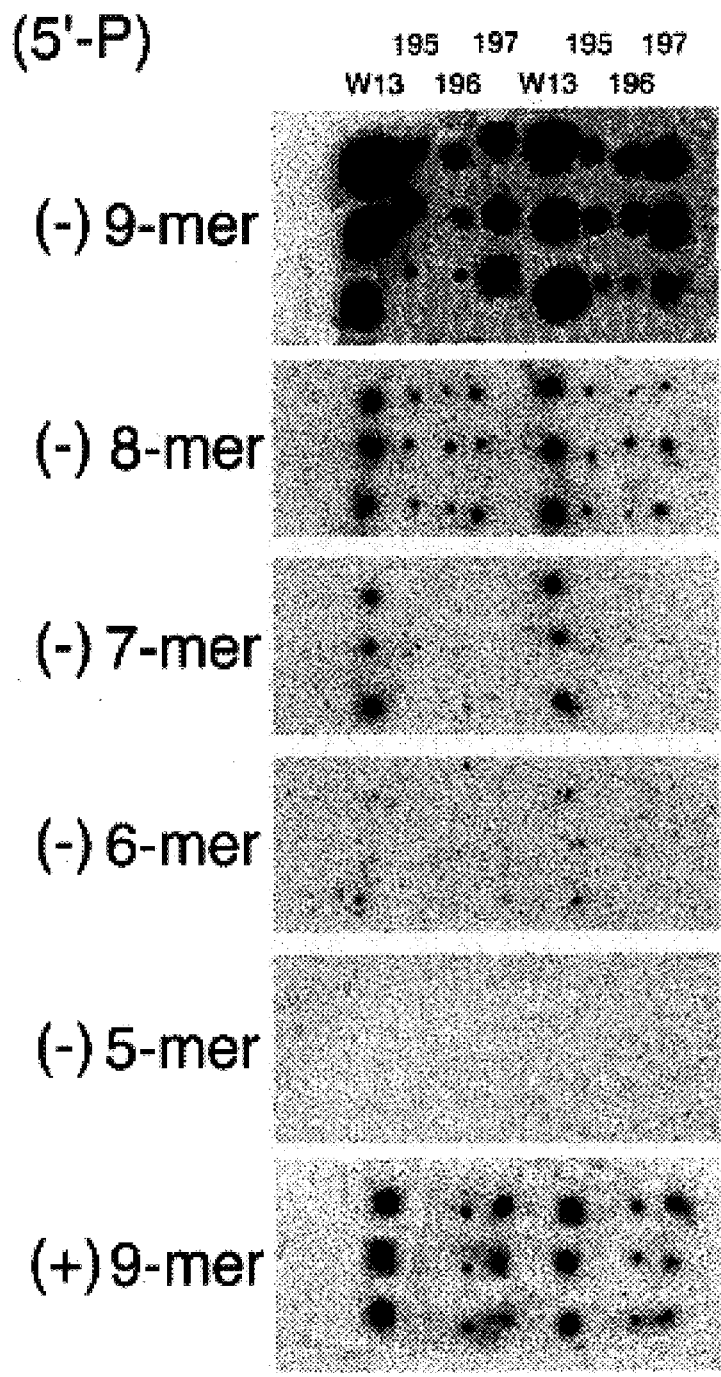
FIG. 11 shows the influence of capture probe length (9 mer down to 5 mer) and terminal phosphorylation on mismatch discrimination using tandem hybridization at 25° C. The results further confirm that improved terminal mismatch discrimination is achieved at lower capture probe length in the tandem hybridization approach of the disclosed invention. The results also show that the hybridization signal decreases with shorter probe length and that the influence of a terminal phosphate group on the capure probe on mismatch discrimination is variable, depending on the mismatch type.

Results of a similar experiment are shown in FIG. 11, in which synthetic target CF179 was hybridized with glass-tethered probes of length ranging from 9 mer down to 5 mer, and in addition, hybridization to arrays of 5'-phosphorylated 9 mer probes was compared with that of the usual unphosphorylated probes. It is again clear that at 25° C. the discrimination of 5'-terminal mismatches (adjacent to the stacking oligomer) improved as the probe length decreased. Hybridization intensity also decreased as a function of probe length, and was undetectable with 5 mer probes. The influence of the 5'-phosphate on mismatch discrimination (lower slide in FIG. 11) is very interesting. Although there was little or no general (consistent) effect on mismatch rejection, there was a differential effect (in opposite directions) on two of the terminal mismatches adjacent to the stacking oligomer. The 5'-phosphate (at least in this sequence context) decreased the stability of the terminal T•T mismatch but increased the stability of the terminal G•T mismatch adjacent to the stacking oligomer. The same differential effect of the 5'-phosphate on the relative stability of T•T and G•T mismatches in these probes was observed when hybridization was carried out at 15° C. and 5° C. (data not shown).

EXAMPLE 9

Effect of Position of Mismatch on Discrimination

Figure 12B:
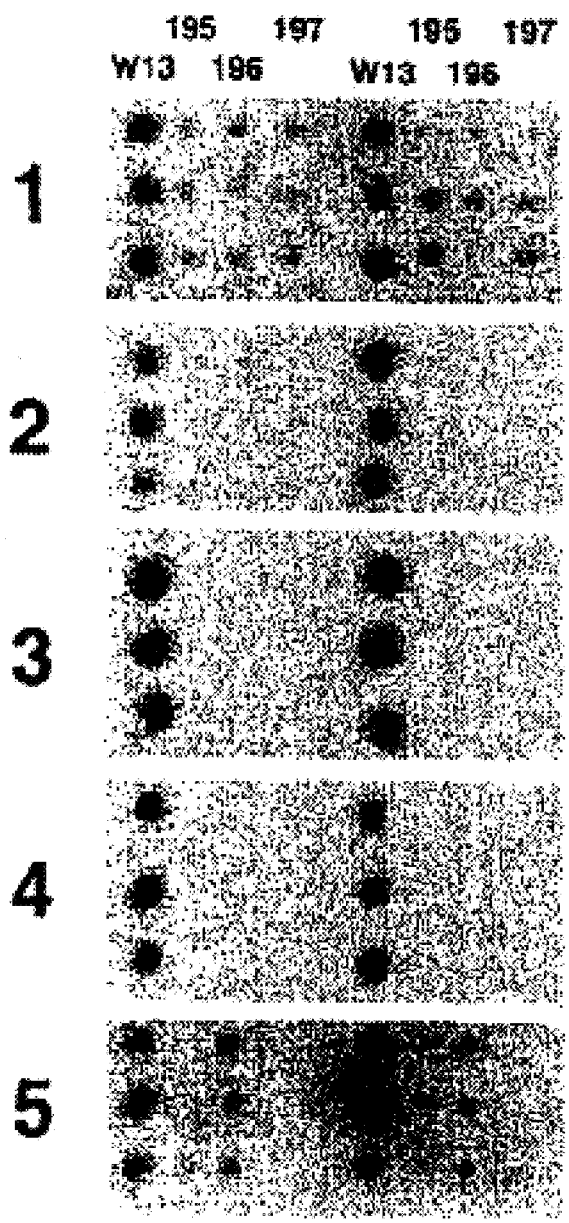
FIG. 12B indicates that with 7 mer glass-tethered capture probes, the best mismatch discrimination is achieved when the capture probes are designed to place the mismatched site at positions 2, 3 and 4 from the free end of the capture probe.

An experiment was carried out to determine the influence of mismatch position within the capture probe on mutation detection by the tandem hybridization approach of the disclosed invention. The results are shown in FIG. 12. The nucleotide sequences of synthetic target CF179 (upper case letters on top line), 5'-$^{32}$P-labeled stacking probe CF164 (upper case italic letters on second line) and 3'-tethered 7 mer capture probes (lower case letters on second line) are shown in FIG. 12A. The 3'-aminopropanol function used to tether the capture probes to the glass slides is indicated by "@." Each of the three possible mismatches are represented, at positions 1, 2, 3, 4 and 5 from the 3' end of the stacking probe CF164 (equivalently, from the 5'-end of the 7 mer capture probe). The synthetic target was preannealed with 5'-$^{32}$P-labeled stacking probe CF164 as described in Example 5, then the mixture was hybridized at 25° C. with arrays of 7 mer capture probes applied to microscope slides, washed, and analyzed by autoradiography as described in earlier examples. The data, shown in FIG. 12B, indicate that the best mismatch discrimination was obtained with 7 mer capture probes designed to place the mismatch site at positions 2, 3 and 4 from the 5'-terminus of the capture probe. These results provide guidance for design of capture probes for optimal base mismatch discrimination in the analysis of DNA sequence variations using the tandem hybridization strategy of the disclosed invention.

EXAMPLE 10

Analysis of DNA Sequence Polymorphisms in Amplified Fragments

In nucleic acid analyses from very small biological samples, a nucleic acid sequence amplification method such as the polymerase chain reaction (PCR), ligase chain reaction (LCR), etc., is preferably used to prepare sufficient target sequence for analysis using the disclosed tandem hybridization strategy. For example, it may be necessary to analyze numerous DNA sequence polymorphisms from a very small number of cells. Highly multiplexed PCR reactions can be used to prepare numerous specific fragments containing several thousand known polymorphic sites. A large collection of target DNA fragments of high genetic complexity can be amplified from a tiny biological sample, and the tandem hybridization strategy of the disclosed invention can then be advantageously used to genotype the fragments, using the general strategy described below.

The genomic DNA is first extracted from the biological sample using standard procedures known to the ordinary artisan. Multiplex PCR is first carried out (using a mixture of PCR primers known to reproducibly amplify a multiplicity of specific genomic fragments) to prepare the desired genomic target sequences which contain the known DNA sequence polymorphisms. The products of individual PCR reactions (each containing from one to numerous primer pairs) may be mixed together to form a complex mixture of amplicons representing up to thousands of polymorphic markers. The PCR fragments can be made single-stranded prior to hybridization, to avoid the re-annealing of complementary target strands, which may compete with the hybridization of target strands to the arrayed capture probes. Single-stranded PCR fragments may be generated by asymetric PCR, by Streptavidin affinity purification when one member of a pair of PCR primers is labeled with biotin, or by exonuclease treatment of duplex PCR fragments, during which half of the target strands are digested. Labeled oligonucleotides, annealing to the target strands immediately adjacent to each polymorphic site, are next mixed with the single-stranded amplified fragments, to introduce the label into the target strands and to serve as the "stacking probes" in the hybridization analysis. Each of these labeled stacking probes, typically about 10–30 nucleotides in length, is designed to bind to a single, unique site in the entire collection of amplified target fragments. Additional labeled or unlabeled auxiliary oligonucleotides may be optionally annealed to the target strands on either side of the polymorphic site, to minimize secondary structure within the single-stranded target or to introduce additional label into target molecules.

For each known DNA sequence polymorphism to be analyzed, a short "capture probe" is synthesized and tethered to the surface of the genosensor chip at a specific site. The capture probes, typically about 6–10 nucleotides in length, are designed to hybridize to the target strand in tandem with the labeled stacking probe, such that mismatched bases are at or near the junction between capture and stacking probes. Each allele of a given sequence polymorphism is represented on the genosensor chip by an allele-specific capture probe. Thus, if there are two alleles at a given polymorphic site, such as for single nucleotide polymorphisms (SNPs) and short insertion/deletion polymorphisms, two allele-specific capture probes are tethered to the hybridization substrate, each at a specific location in the array. The capture probes may be tethered to glass surfaces via reaction of a 5'-terminal modification with the glass (such as described in Example 1) or via immobilization at the 3'-end as described in Example 5. The practitioner is not limited to the oligonucleotide attachment methods cited herein, since many alternative immobilization methods have been described in the prior art which may equally serve in the auxiliary oligonucleotide/tandem hybridization strategy of the disclosed invention. Similarly, the practitioner is not restricted to immobilization of oligonucleotide probes to glass surfaces in order to implement the disclosed invention, since one skilled in the art may readily adapt any of the numerous attachment chemistries described in the prior art for linking synthethic DNA probes to solid supports, including plastics, silicon, gold, platinum, any silanized solid surface, polymer matrix, membranes, etc.

A cocktail of labeled stacking probes (and optionally, additional labeled or unlabeled auxiliary oligonucleotides) is mixed with the amplified DNA, then the mixture is hybridized to an array of immobilized short allele-specific capture probes under conditions described in Examples 2–9. The resulting quantitative hybridization fingerprint reveals the allele status at each polymorphic site. For a given polymorphic site, the relative hybridization intensity at positions in the genosensor array containing the different allele-specific capture probes will reveal which alleles are present, and whether the sample is homozygous or heterozygous at the polymorphic site. By using complex mixtures of PCR amplicons and a corresponding complex cocktail of labeled stacking probes, it is possible to obtain, in a single hybridization experiment, a genotype representing hundreds to many thousands of DNA markers.

EXAMPLE 11

Analysis of Heat-denatured Duplex DNA without Isolation of Single Strands

An important aspect of the disclosed invention is the use of auxiliary oligonucleotides, annealed to the nucleic acid target strand in the region of the binding site of the surface-tethered capture probe, to minimize the formation of secondary or higher order structure (such as stem-loops or hairpins) which may make the target sequence unavailable for hybridization to the surface-tethered probe, and also to inhibit reannealing of complementary strands of a denatured duplex target fragment, which would likewise make the target sequence unavailable for hybridization to the capture probe. This use of auxiliary oligonucleotides is therefore intended to facilitate the analysis of heat-denatured duplex DNA fragments by oligonucleotide hybridization, eliminating the need to physically isolate single-stranded target DNA prior to hybridization analysis.

Figure 13A:
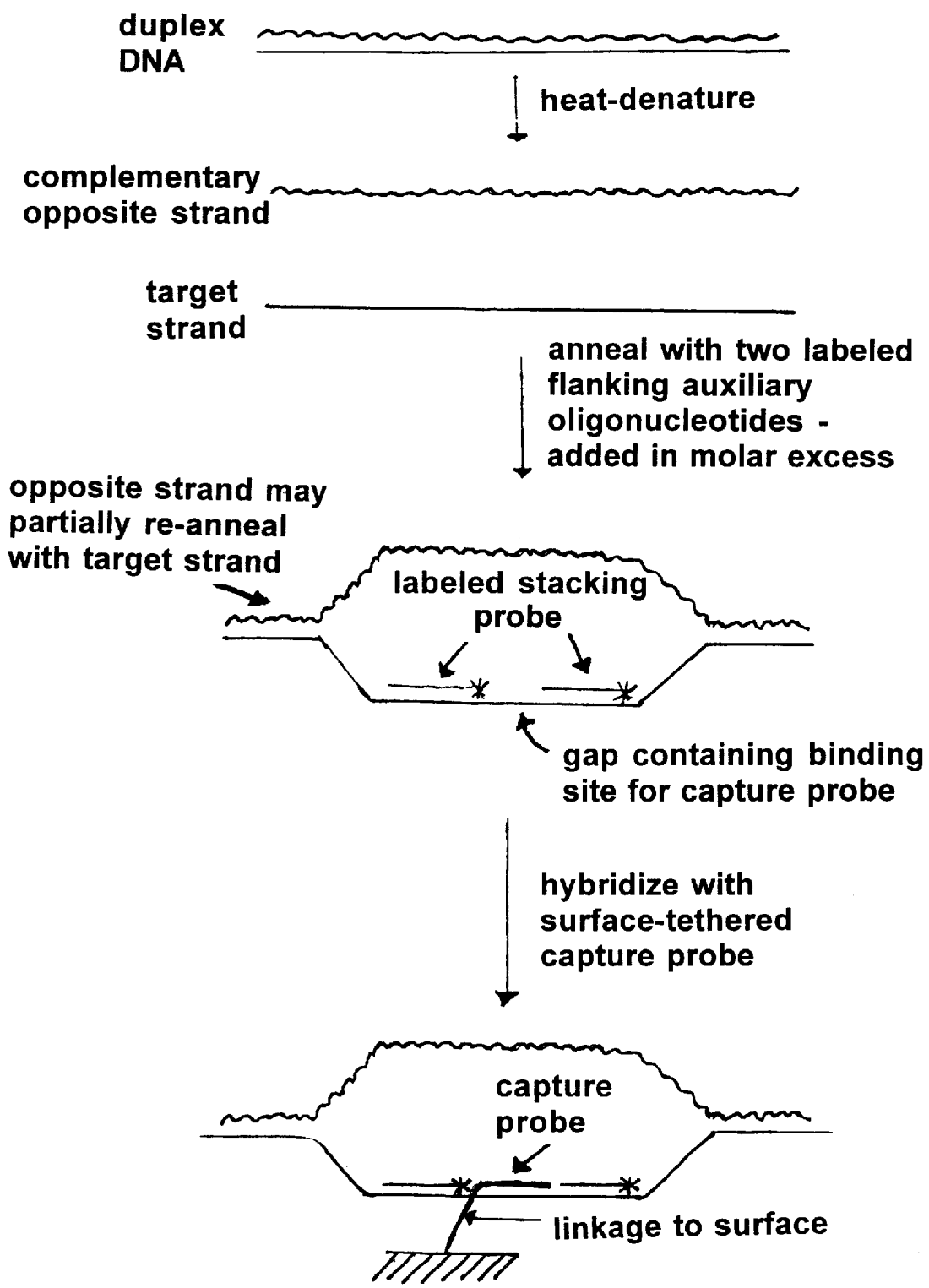
FIG. 13 illustrates in schematic form the utility of annealing auxiliary oligonucleotides on both sides of the site within the target strand hybridizing to the capture probe, and optionally to the opposite strand, to enable analysis of denatured double-stranded DNA by the disclosed tandem hybridization invention, without prior isolation of single-stranded target DNA.

The use of auxiliary oligonucleotides to facilitate hybridization analysis of denatured duplex DNA is illustrated schematically in FIG. 13. In the basic strategy mentioned previously, illustrated in FIG. 13A, two auxiliary oligonucleotides, complementary to the target sequence on both sides of the hybridization site of the capture probe, are preannealed in molar excess to the heat-denatured DNA target. The presence of a molar excess of these auxiliary oligonucleotides will impede the reannealing of complementary analyte strands, as well as minimizing secondary structure within the target strand as discussed above. One or both of the flanking auxiliary oligonucleotides may be labeled, and one or both of them may serve as "stacking probes," hybridizing in tandem with the capture probe. The flanking auxiliary oligonucleotides may alternatively be added to the heat-denatured target DNA at about the time of initiation of the hybridization reaction to the surface-tethered capture probe. The length of auxiliary oligonucleotides flanking the capture probe may vary over a wide range, depending on the genetic complexity of the DNA analyte. For analysis of a single denatured PCR products or a mixture of several PCR products (up to about ten), the flanking auxiliary oligonucleotides may be 7 mer or longer. For a highly multiplexed mixture of PCR products (up to about ten thousand specific fragments) or for genomic DNA, the flanking auxiliary oligonucleotides may be of length about 10 mer to about 50 mer but preferably of length selected to ensure binding to a unique site within a target sequence of a given genetic complexity, as disclosed previously. The use of labeled stacking probes on both sides of the capture probe, is conceptually related to the use of a single longer stacking probe (of length sufficient to ensure binding to the target sequence at a unique location), except that the longer stacking probe is divided into two sections, contiguously stacking to both sides of the capture probe. For example, if a 7 mer capture probe plus two 7 mer stacking probes, contiguously stacking on both sides of the capture probe are used, the total length of contiguously stacked duplex DNA formed at the analysis site will be 21 mer, similar to that formed using a 7 mer capture probe plus a single 14 mer stacking probe. In model mutation detection experiments employing the above "double stacking probe" approach, the inventors have achieved excellent mismatch discrimination using 7 mer and 8 mer capture probes, equal or better than achieved using a single stacking probe, and in this embodiment of the invention, best mismatch discrimination was achieved when the mismatch was located near the center of the capture probe.

Figure 13B:
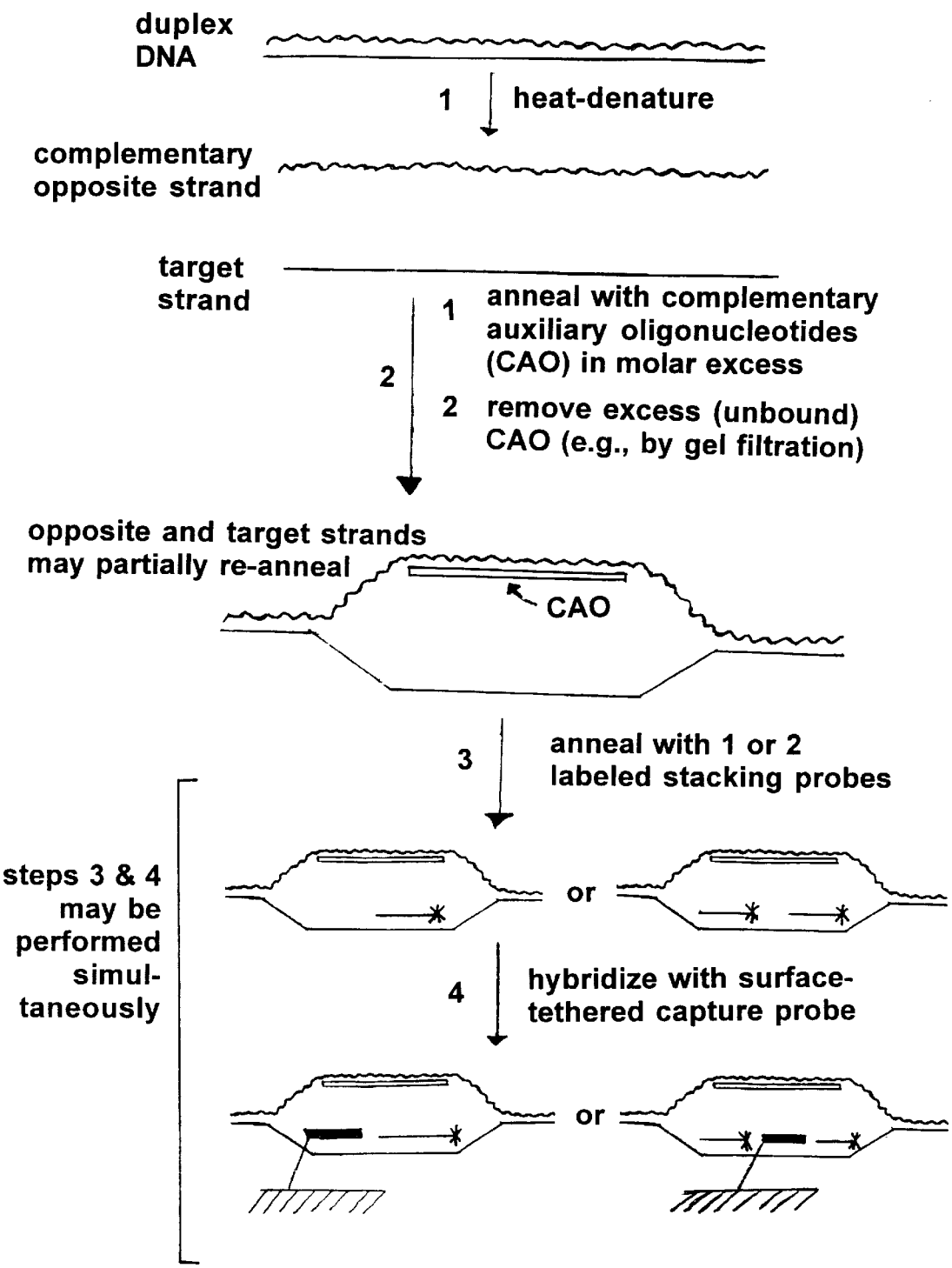

In a related approach, depicted in FIG. 13B, a third, longer "complementary auxiliary oligonucleotide," which binds to the opposite strand as the capture and stacking probes, is preannealed in molar excess to the heat-denatured target DNA, then the excess of this longer complementary auxiliary oligonucleotide is removed (eg., using gel filtration) prior to addition of the stacking probes and hybridization to the surface-tethered capture probe. The latter technique may be employed whether there is a single stacking probe or flanking stacking/auxiliary probes, and the length of the "complementary auxiliary oligonucleotide" is preferably at least equal to the combined length of stacking/auxiliary probes and capture probe. For example, if the capture probe is 8 mer and two flanking stacking probes are 11 mer and 15 mer, the "complementary auxiliary oligonucleotide" is preferably at least 34 bases long, the length of contiguously stacked duplex region formed by capture and capture probes.

EXAMPLE 12

Analysis of Gene Expression Using PCR Amplification

For analysis of expressed sequences in small biological samples, mRNA is extracted from the biological sample, converted to DNA using reverse transcriptase, then PCR or other amplification strategies can be used to prepare fragments whose relative abundance reflect the relative abundance of specific mRNA species in the original mRNA sample: Sequence-targeted multiplex PCR can be used to amplify one or more known sequences within each transcript; arbitrary sequence PCR can be used to prepare fragments representing a random subset of sequences within the mRNA population; or oligo(dT) primers can be used in combination with sequence-targeted or arbitrary sequence primers, to amplify 3'-untranslated regions of the mRNA population. As in the analysis of DNA sequence polymorphisms (Example 10), single-stranded PCR fragments may be generated prior to hybridization to the genosensor array. Alternatively, preannealing of PCR fragments with a molar excess of multiple auxiliary oligonucleotides to prevent reannealing of the target in the region of analysis (as described in Example 11) can be employed to enable direct analysis of duplex PCR fragments without isolation of single strands. Each gene transcript is represented in the genosensor array by a short "capture probe" which is designed to hybridize to the corresponding target strand (derived from the relevant gene transcript) in tandem with the corresponding labeled "stacking probe." The capture probes and stacking probes can be designed to analyze a specific subset of genes, or a complete set of potential transcripts of an organism, depending on the purpose of the analysis and the extent to which sequence information is available for the organism of interest. This approach can also be used for mixed populations of organisms, provided that sequence information is known for the genes and species of interest.

EXAMPLE 13

Direct Analysis of Complex Nucleic Acid Sequences without PCR

The nucleic acid analyses described in Examples 1–4 and 10–12 represent special circumstances, under which the quantity of nucleic acid available from a small biological sample is insufficient for direct genosensor analysis, and amplification of target strands by PCR or other target enhancement methods is therefore required. In many types of nucleic acid analysis, however, a sufficient quantity of nucleic acid will be available for direct analysis using the tandem hybridization strategy of the disclosed invention, without the need to perform a costly and time consuming initial step of DNA amplification. Avoidance of PCR amplification also eliminates the occurrence of a variety of artifacts (eg., self-priming/primer dimer, random priming, amplification of contaminant sequences, and other causes of irreproducible or misleading results), which are well known problems in PCR applications. Examples of nucleic acid sequence analyses that may be performed directly using the tandem hybridization strategy of the disclosed invention, without employing DNA amplification, include DNA marker analysis, genotyping, mutational screening, microbial identification and gene expression/mRNA profiling using nucleic acids extracted from cultured organisms, tissue biopsies, or biological samples collected from plentiful agricultural stocks or natural ecosystems.

The critical consideration which enables direct application of the disclosed tandem hybridization approach without DNA amplification is the appropriate design of the labeled stacking probes, so that the hybridization is specifically targeted to unique sites within nucleic acid analytes of high genetic complexity. To achieve the required site specificity with a nucleic acid sample such as total genomic DNA or bulk mRNA or cDNA derived therefrom, a collection of labeled "stacking probes" is synthesized, of sufficient length (typically about 10–30 bases, the exact length depending on the genetic complexity of the nucleic acid analyte) to ensure that each stacking probe anneals to a unique position within the entire nucleic acid sample.

The labeled stacking probes are added to the nucleic acid sample, and the mixture is hybridized with the array of short capture probes (typically about 6–10 bases in length), each designed to bind to a specific target sequence, in tandem with the appropriate stacking probe. The capture probes may be designed to bind to the target on either the 5'-side or 3'-side of the tandemly hybridizing "stacking probe." The labeled stacking probes are typically preannealed to the nucleic acid target strands, but alternatively, may be added to the analyte at the beginning of hybridization to the oligonucleotide array, or even after application of analyte to the array. The hybridization is carried out under conditions such that significant binding of the nucleic acid analyte to the oligonucleotide array will occur only if the capture probe and stacking probe hybridize in tandem with the target strand. For example, under typical hybridization conditions (6×SSC or 3M TMAC at 45° C.) a 7 mer capture probe will not form a stable duplex structure with isolated complementary sequences within a nucleic acid sample, even though the 7 mer will likely have numerous complements within a sample of high genetic complexity, but the short capture probe will hybridize specifically with the nucleic acid target at the site uniquely placed into register for contiguous stacking hybridization, via annealing of a longer stacking probe.

The experimental strategy described above may be used with flat surface genosensor arrays if sufficient time is allowed for hybridization, considering the very low concentration of individual short sequences (combined length of tandemly hybridizing capture and stacking probes) within a nucleic acid sample of high genetic complexity. A preferred hybridization substrate, however, for direct nucleic acid analysis using the disclosed tandem hybridization method is the flowthrough genosensor chip (Beattie et al, *Clin. Chem.* 41:700–706, 1995; Doktycz & Beattie, In *Automated Technologies for Genome Characterization*, Beugelsdiik, Ed., J. Wiley & Sons, Inc., pp. 205–225, 1997; Beattie et al, In *Pharmacogenetics: Bridging the Gap Between Basic Science and Clinical Application, IBC Biomedical Library*, Schlegel, Ed., Southborough, Mass., pp. xx–yy, 1996), in which the nucleic acid analyte is flowed through a porous silicon or microchannel glass chip, in which the capture probes are tethered within patches of densely packed channels connecting the two faces of the chip. The flowthrough configuration is particularly preferred for analysis of heat-denatured dilute solutions of nucleic acids, and offers improved sensitivity and dynamic range, compared with the flat surface genosensor configuration. Other hybridization substrates of high effective surface area may likewise serve to facilitate analysis of complex nucleic acid mixtures using the disclosed tandem hybridization strategy, including rigid fritted materials, rigid or flexible membrane materials, layers of matted fibrous materials, woven fabric materials, micromachined silicon structures, porous plastics, polymer gel matrices, etc.

For direct genotyping or mutational scanning of total genomic DNA, the sample is preferably fragmented by sonication, microwave treatment or by enzymatic or chemical degradation, mixed with the appropriate set of labeled stacking probes, then hybridized with the allele-specific capture probes arrayed across the genosensor chip. As discussed in Example 12, the relative intensity of hybridization signals at each position across the chip reveals the allelic status at each site, and the procedure can be used to simultaneously analyze thousands of known DNA sequence variations.

For direct transcriptional profiling, mRNA is extracted from the biological sample, optionally converted to cDNA, heat-denatured and mixed with the desired set of gene-specific labeled stacking probes (typically of length 10–30 bases), then hybridized with the appropriate set of arrayed capture probes (typically of length 6–10 bases) specifically designed to hybridize to the target strand in tandem with the labeled probes.

EXAMPLE 14

Direct Analysis of Expressed Sequences or DNA Sequence Polymorphisms Using "Universal" Labeled Stacking Probes If the labeled stacking probe is designed to anneal to sequences present in all target molecules, such as the poly (A) tail in mRNA or repetitive sequence elements in genomic DNA, then a single labeled stacking probe can be preannealed to the target nucleic acid, and the mixture hybridized to an array of surface-tethered capture probes which uniquely represent each sequence analyzed.

For example, a universal labeled stacking probe, comprising oligo(dT) (for direct analysis of poly(A)$^+$ mRNA) or oligo(dA) (for analysis of reverse-transcribed cDNA) plus 1–3 redundant residues (mixture of all 4 bases or universal base analog) extending into the expressed sequence of mRNA or cDNA can be preannealed with the mRNA or cDNA, and the mixture hybridized to an array of transcript-specific capture probes designed to bind to the target in tandem with the universal labeled probe. In this special embodiment the capture probes are preferably longer (typically about 10–15 bases) than when the stacking probe is gene-specific, to ensure that the capture probe binds to a unique transcript. Thus, if the universal labeled stacking probe is used, the required site-specificity of the hybridization analysis must be achieved using capture probes of length sufficient to enable each capture probe to hybridize uniquely to a single target sequence among all expressed sequences present in the sample. The relative hybridization intensity at each position in the array will then reflect the relative abundance of expressed sequences in the sample.

A similar strategy could be used for analysis of DNA sequence polymorphisms flanking repetitive sequences in genomic DNA. In this case the universal labeled probe could contain a sequence (or mixture of closely related "consensus sequences") at the beginning or end of a repetitive sequence element such as SINE (including Alu), LINE, or "short tandem repeat" ("microsatellite") sequence, plus a short redundant sequence (string of mixed bases or universal base, as in the polA/mRNA embodiment) to position the labeled probe at the junction of each member of the repetitive sequence element in genomic DNA. The array of surface-tethered capture probes would then correspond to DNA sequence polymorphisms flanking the repetitive sequence elements. As in Example 14, the capture probes would need to be long enough to hybridize to a unique site within the genomic DNA.

Finally, the approach described above may be similarly used to analyze mitochondrial or chloroplast DNA in eukaryotic organisms, where stretches of conserved sequence are flanked by highly variable sequence in a high copy number extranuclear organelle. In these cases the universal labeled tandem probes will be annealed to the conserved sequence and the allele-specific short capture probes will hybridize in tandem with the variable sequence adjacent to the universal stacking probes.

EXAMPLE 15

Microbial Identification

The tandem hybridization method can also be used to unambiguously detect and identify bacterial, viral or other microbial species or strains on the basis of known, unique features of nucleic acid sequences. As discussed in Example 10, if the biological sample contains too little genetic material for direct analysis by the genosensor array, a target amplification method such as multiplex PCR can first be used to prepare a collection of genomic regions known to contain unique sequences. If sufficient biological material is available, such as cultured cells or large clinical sample, the nucleic acids can be directly analyzed to identify the species or strain, without using PCR. As discussed in Example 13, flat surface oligonucleotide arrays may be used for the tandem hybridization strategy with DNA targets of high genetic complexity, provided sufficient hybridization time is allowed, however a flowthrough hybridization substrate is preferable when the concentration of target sequence complementary to the surface-tethered capture probes is very low.

For microbial identification the analysis can be targeted to the well known highly variable regions of 16S ribosomal RNA genes, present in multiple copies per cell. For dilute samples, such as typical clinical or environmental specimens, PCR primers targeted to conserved regions of bacterial 16S rRNA genes can be used to amplify 16S rRNA gene fragments from DNA extracted from essentially any bacteria. For cultured bacteria the amplification step may be unnecessary; DNA or RNA extracted from the culture may be analyzed directly. Labeled stacking probes, of length sufficient to insure specific hybridization to the conserved 16S rRNA or rRNA gene sequence flanking the variable 16S rRNA or rRNA gene sequence, are mixed with the extracted DNA or RNA, then the mixture is hybridized to an array of species- or strain-specific capture probes, hybridizing to the target strands in tandem with the corresponding labeled stacking probes. The analysis is preferably simplified by using a small number of "universal" or "group-specific" labeled stacking probes, designed to hybridize to conserved regions of 16S rRNA genes, immediately adjacent to the hypervariable regions to which the species- or strain-specific capture probes would be targeted. The use of several conserved stacking probes, together with a large collection of species- or strain-specific tandemly hybridizing capture probes, will produce a hybridization fingerprint which will unambiguously identify the microorganism in a pure culture, or simultaneously identify numerous species or strains in a mixed culture or environmental sample, and also reveal the relative abundance of different microorganisms in a mixed sample.

The tandem hybridization strategy can also be used in viral nucleic acid analysis, for example, in the detection and typing of human papilloma virus from a tissue specimen. In this case, multiplex PCR is first used to specifically amplify one or more fragments from any of the known HPV genotypes. HPV type-specific combinations of labeled stacking probes and surface-tethered capture probes, designed such that each HPV genotype will bind to a specific site within the genosensor array, are then used to reveal the HPV genotype in a single hybridization assay.

EXAMPLE 16

Tandem Hybridization Using Universal Oligonucleotide Arrays

The tandem hybridization approach of the disclosed invention may be used with "universal" oligonucleotide arrays containing all sequences of a given oligomer length, for example an array of all 4,096 hexamer (6 mer) capture probes, all 16,384 heptamer (7 mer) capture probes, all 65,536 octamer (8 mer) capture probes, etc. The "universal" array of capture probes to be used in the tandem hybridization strategy may also comprise a mixture of oligonucleotide lengths, selected from the sets of all sequences of each given length, to minimize the effects of base composition on duplex stability and thus enable any of the capture probes to function under a single hybridization condition. For example, a modified 7 mer array may contain some 8 mers and 9 mers in which the A-rich, T-rich or AT-rich sequences contain one or more additional nucleotides added (onto the end opposite from that which will abut with the stacking probe) to increase the stability of their dupleces (formed with complementary target sequences) closer to that of the GC-rich 7 mer capture probes within the "universal" array. The "universal" array of capture probes may in addition be edited to remove sequences that are judged to be problematic or uninformative, such as repetitive sequences.

The advantage of a "universal" array of capture probes is that a single array may be mass-produced and used for a large variety of nucleic acid analytes, together with labeled stacking probes designed for each type of assay. For example, a universal array of short capture probes may be used with a mixture of gene-specific labeled stacking probes (each designed to represent a known, unique coding sequence or open reading frame) to obtain a gene expression (transcriptional) profile using bulk mRNA or cDNA, whereby the quantitative hybridization pattern across the array reflects the relative abundance of each expressed sequence, thus the relative activity of different genes. For gene expression profiling in higher eukaryotes, a universal capture probe array may be used with the universal labeled stacking probe mixture (as described in Example 14) which binds to the polyA tail of each mRNA (or to the polyT tail of the corresponding reverse transcribed cDNA.

Similarly, a universal array of capture probes may be used for simultaneous analysis of numerous mutations or DNA sequence polymorphisms, using a mixture of labeled stacking probes, each designed to anneal to a target nucleic acid at a unique site, adjacent to the site of a known mutation or polymorphism. In the latter example, the allelic status for each mutational site or polymorphism (wild-type, known mutation, polymorphic marker allele, and homozygous versus heterozygous condition) will be revealed from the quantitative hybridization pattern. A universal capture probe array may be used in combination with a universal stacking probe comprised of repetitive sequences (eg, SINE, STRP, etc.), to simultaneously analyze numerous DNA sequence polymorphisms flanking repetitive sequences in genomic DNA, as described in Example 14.

The use of universal oligonucleotide arrays together with contiguous stacking hybridization has been previously proposed by the Mirzabekov laboratory for sequencing by hybridization, however as discussed previously, the stacking hybridization approach of the invention disclosed herein differs in several important aspects from that of Mirzabekov. For example, each of the stacking probes used herein are of longer length (than those employed by Mirzabekov), designed to hybridize at a single unique position within a nucleic acid analyte of high genetic complexity. Furthermore, the stacking probes used herein are added to the nucleic acid analyte prior to hybridization to the array, whereas those employed by Mirzabekov are added in one or more additional cycles of hybridization, following the initial binding of target strand to the array of capture probes. Finally, the use of long stacking probes (as disclosed herein) is expected to minimize the effects of base composition on duplex stability, improving the ability of all short capture probes within a univeral array to hybridize with a complementary sequence within the target nucleic acid, since the major duplex stability in the stacked configuration is derived from the stability of the longer stacking probe.

EXAMPLE 17

Analysis of Short Tandem Repeat Polymorphisms (STRPs)

Figure 14A:
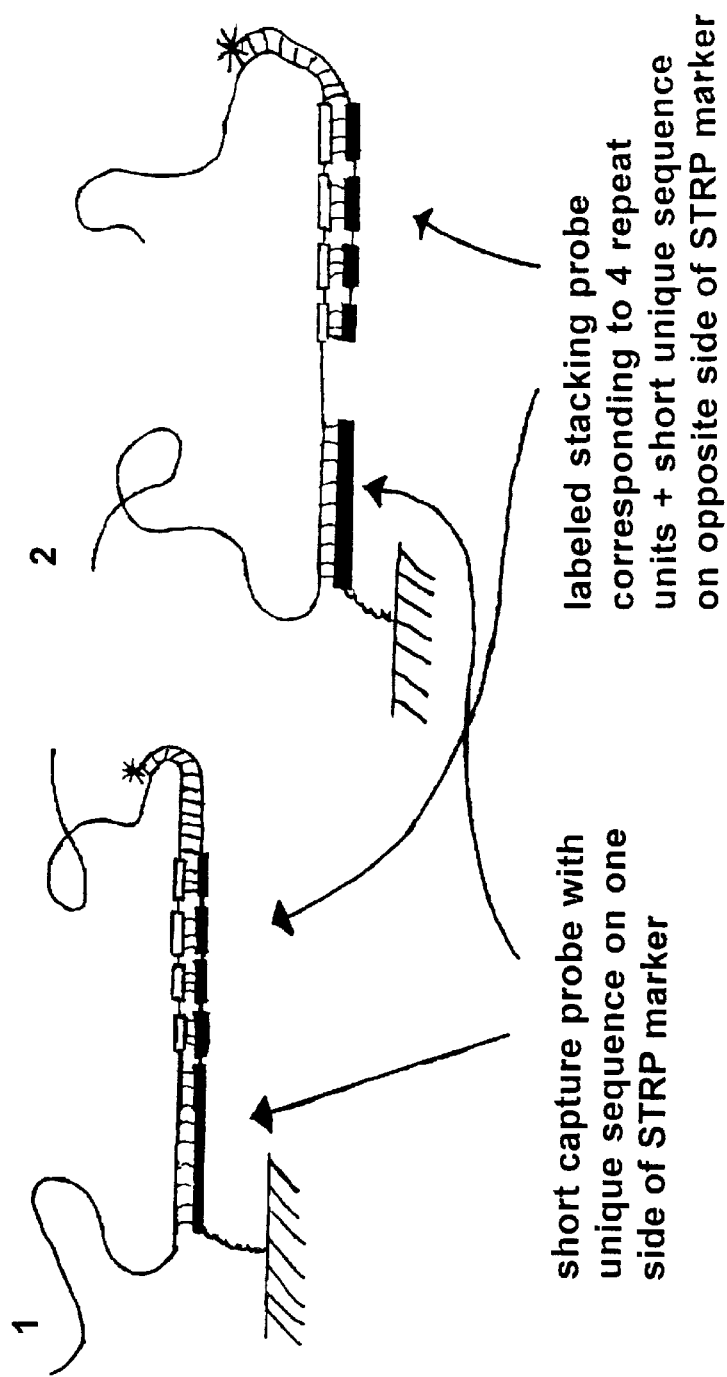
In FIG. 14A each STRP marker is represented by a capture probe tethered to a specific location on the oligonucleotide array. A different label for each STRP allele analyzed in a given hybridization reaction is needed. For markers containing numerous alleles, several hybridization reactions may be performed. In 1 the target sequence contains four repeat units; the stacking probe hybridizes in tandem with the capture probe yielding a positive hybridization signal with the label (*). In 2 the target sequence contains five repeat units; no stabilizing stacking interaction occurs yielding little or no hybridization signal with the label (*).

The tandem hybridization approach of the disclosed invention may be used to analyze the most ubiquitous type of DNA sequence polymorphism, STRPs, also known as "microsatellites" and "variable number tandem repeats" (VNTRs). Two embodiments are disclosed, as illustrated schematically in FIG. 14. FIG. 14A illustrates schematically the use of allele-specific labeled stacking probes for STRP analysis. An array of short (preferably 7 mer–9 mer) capture probes is used, representing the nonrepetitive (unique) sequences known to be flanking each of the STRP markers to be analyzed. Alternatively, the univeral array of capture probes, as disclosed in Example 16, may be used. For each STRP allele of the set of STRP markers to be analyzed, a labeled stacking probe is used, which contains a nonrepetitive (unique) sequence at one end (functioning to position the stacking probe at the opposite side of the STRP marker from the likewise "positioned" capture probe), plus a specific number of short tandem repeat elements. As in the general scheme of tandem hybridization of the disclosed invention, binding of label (corresponding to a given STRP allele) to the array position containing the capture probe for a given marker will occur only if there is contiguous stacking between capture probe and stacking probe hybridized to the DNA target. In the example illustrated in FIG. 14A, a stacking probe containing four repeat units will stabilize the binding of label to the surface-tethered stacking probe if the target DNA contains four repeat units but not if the target DNA contains five repeat units (in which case a gap will exist between stacking and capture probes). In the use of allele-specific stacking probes, each STRP marker is represented by a capture probe tethered to a specific location on the array, bearing a nonrepetitive sequence at one end of the marker, and each STRP allele is represented by a labeled stacking probe bearing a nonrepetitive sequence at the other end of the marker, plus a specific number of short tandem repeat units. For this embodiment a different (distinguishable) label is needed for each STRP marker allele analyzed in a given hybridization reaction. Several separate hybridization reactions may be employed for analysis of STRP markers having more alleles than there are distinguishable labels.

Figure 14B:
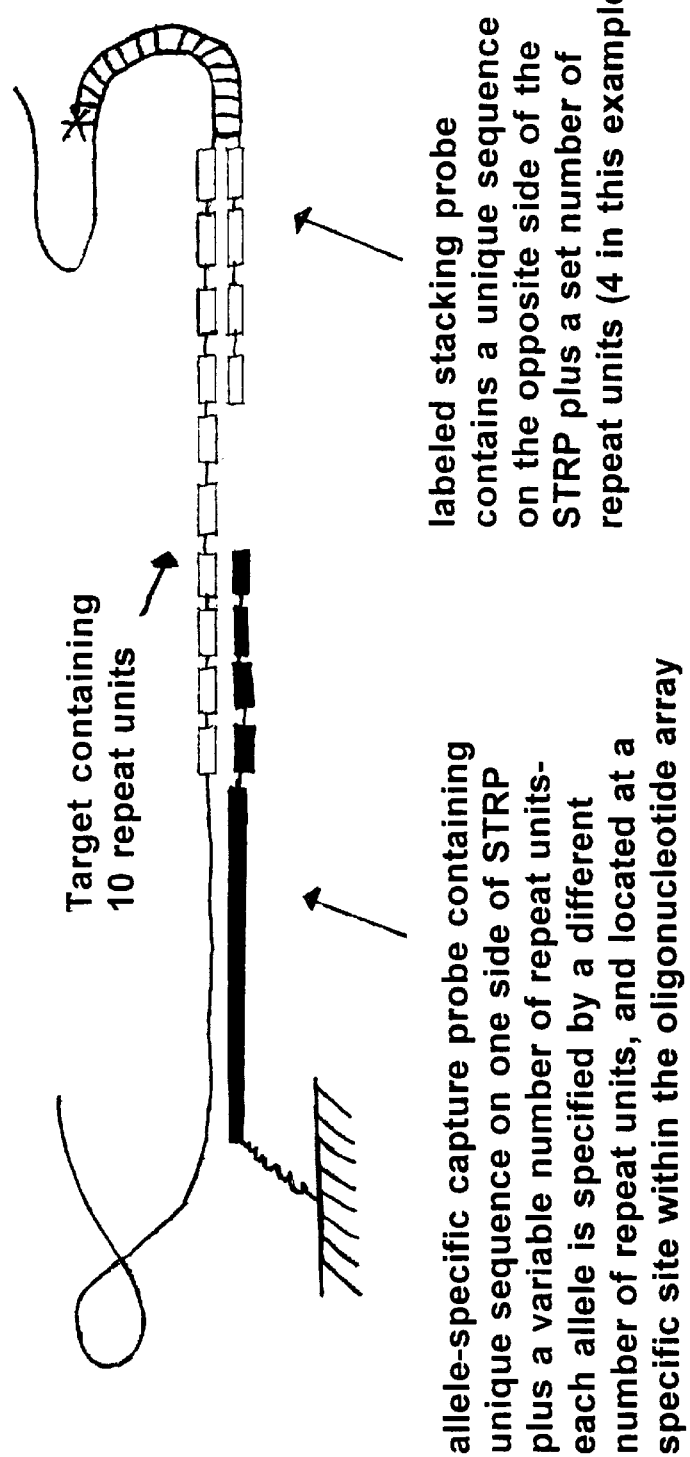
In FIG. 14B the capture probe shown will give contiguous stacking with the labeled stacking probe only if the target contains eight repeat units; thus, little or no label binds at this site in the array. The target shown will give a hybridization signal at an array location containing a six-repeat capture probe.

An embodiment in which allele-specific capture probes are used for STRP analysis is illustrated in FIG. 14B. The approach is similar to that illustrated in FIG. 14A, except that for each STRP marker a single labeled stacking probe is used, containing a nonrepetitive "anchor" sequence flanking one side of the marker, plus a set number of short tandem repeat units (four in the example illustrated), and the different STRP alleles are represented by capture probes (tethered to the surface at specific locations within the array) containing a short nonrepetitive (unique) "anchor sequence" (on the other side of the marker from that of the stacking probe), plus a variable number of repeat units. In the example shown (a marker with ten repeat units) a capture probe bearing four repeat units would not stack contiguously with the stacking probe bearing four repeat units, thus there would be little or no binding of label to this array position (with the target bearing 10 repeat units), however, the label would be bound at a position in the array containing a capture probe bearing six repeat units, and if the target contained 8 repeat units, the label would bind (due to contiguous stacking) to the array position containing the capture probe with four repeat units, hybridized in tandem with a stacking probe bearing four repeat units. In the enbodiment illustrated in FIG. 14B each STRP marker allele is represented at a different position within the array of capture probes. The feature of using nonrepetitive "positioning" sequences (flanking a given STRP marker) in both capture probes and stacking probe for a given marker enables analysis of multiple alleles for each marker. For simultaneous analysis of numerous STRP markers (located at different sites within a genome), each marker analyzed will have a labeled stacking probe containing a nonrepetitive sequence flanking one side of the marker, and different alleles are detected from the position within the array (among the capture probes bearing variable number repeat units for that marker) to which label is bound.

In addition to using allele-specific stacking probes or allele-specific capture probes as illustrated in FIGS. 14A and 14B, a combination of the two approaches may be used, in which both capture probes and stacking probes contain a nonrepetitive (unique) sequence flanking the STRP marker, plus a variable number of repeat units. Furthermore, a universal array of capture probes (as described in Example 16) may be used for STRP marker analysis, in place of arrays of marker-specific capture probes, when allele-specific stacking probes are employed.

EXAMPLE 18

Figure 15A:
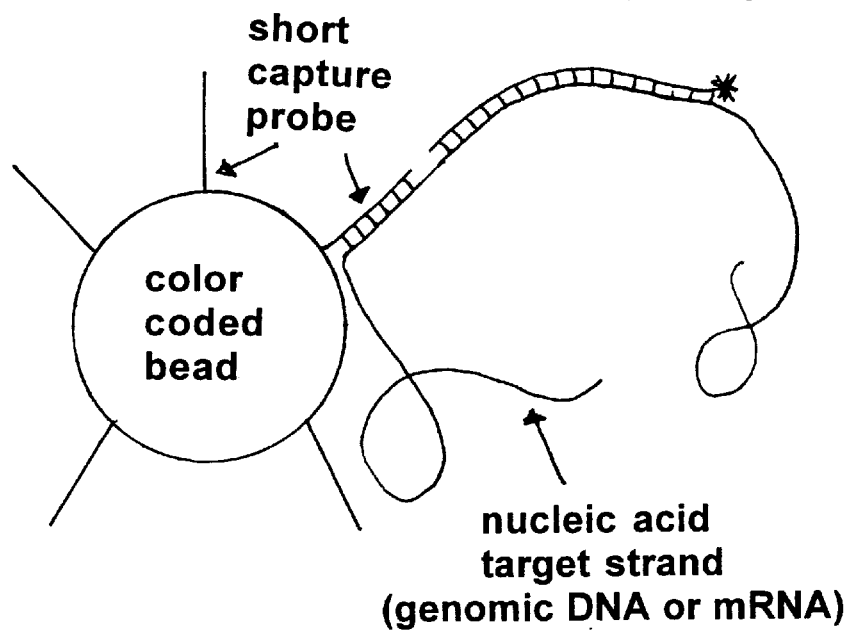
In FIG. 15A the short capture probe on the color-coded bead is specific for a known sequence at the 3'-end of mRNA. For genotyping and mutation analysis, the bead-immobilized capture probe is allele-specific, designed to hybridize in tandem with the longer labeled stacking probe designed for the sequence polymorphism or mutation. The longer labeled stacking probe may be gene-specific; ie, one labeled stacking probe for each sequence region analyzed, or it may be a universal stacking probe; e.g., oligo(dT)-NNN for analysis of 3'-end of eukaryotic mRNAs. The relative level of binding of label to each color-coded bead quantitated by flow cytometric with spectral analysis indicates the relative abundance of mRNA species (transcriptional profiling) or the allelic status at each DNA marker or mutational site.
Figure 15B:
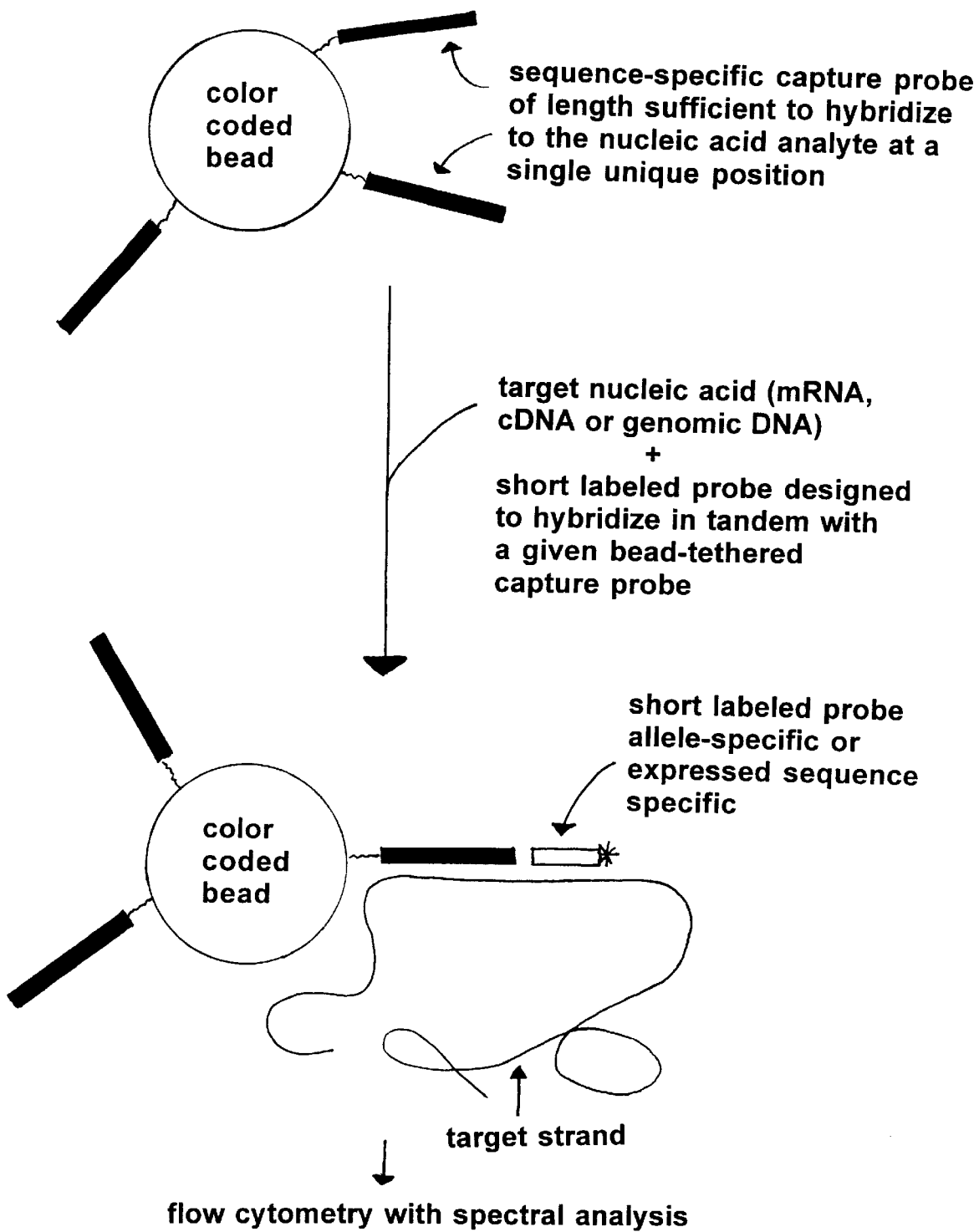
In FIG. 15B a sequence-specific capture probe of a length sufficient to hybridize to the nucleic acid analyte at a single unique position hybridizes with the target nucleic acid in conjunction with a short labeled probe which itself is designed to hybridize in tandem with the given bead-tethered capture probe. As in FIG. 15A, the relative level of label associated with each color-coded bead quantitated by flow cytometry with spectral analysis is indicative of the relative abundance of mRNA/cDNA species, or relative abundance of different sequence variants.

Analysis of Nucleic Acids Using Tandem Hybridization on Color-coded Microspheres and Flow Cytometric Detection In Examples of the disclosed stacking hybridization invention described above, arrays of surface-tethered capture probes are employed, wherein the quantitative hybridization pattern across the array reveals the desired sequence information about the nucleic acid analyte. The stacking hybridization approach of the disclosed invention is equally applicable to "bead technology" in which different capture probe sequences are tethered to microspheres which are distinguishable by any measurable (detectable) unique physical or chemical property associated with each bead, such as size, shape, mass, spectral profile, chemical reactivity, electronic properties, etc. A specific example of this approach is illustrated in FIGS. 15A and 15B, wherein the FlowMetrix system of Luminex Corp., invloving flow cytometry with spectral analysis of color-coded latex microspheres (McDade and Fulton, Medical Device & Diagnostic Industry, April 1997) is employed to enable multiplex analysis of numerous hybridization reactions. This Example is intended to illustrate only one possible combination of stacking hybridization with bead technology. It will be evident to one skilled in the art that as indicated above, other physical or chemical properties of the beads (besides luminescence spectral properties used in the FlowMetrix system) may be advantageously employed to distinguish and quantitate the binding of analyte nucleic acid to specific capture probes tethered to distinguishable beads. Two embodiments of the combination of tandem hybridization with bead technology are illustrated schematically in FIGS. 15A and 15B. FIG. 15A shows the basic approach to genotyping, mutational analysis and gene expression profiling. The nucleic acid analyte is annealed with a labeled stacking probe, of sequence and length designed to bind to a unique position within the analyte nucleic acid. Each short capture probe sequence is immobilized to a specific color-coded bead, and upon hybridization with the stacking probe/target strand, the label will bind to the bead only when the stacking probe is hybridized to the target sequence in tandem with the capture probe. For genotyping and mutation analysis, allele-specific capture probes (each associated with a different color-coded bead) are hybridized with genomic DNA (or mixture of PCR products) preannealed with a mixture of stacking probes (binding to the target DNA adjacent to a set of polymorphic or mutation-bearing sites). The quantity of label associated with each color-coded bead (quantitatively determined using flow cytometry with spectral analysis of individual beads streaming past the detector window) will reveal the allele status at each marker or mutational site analyzed. If expressed sequence-specific stacking and capture probes are used with mRNA or cDNA analyte (as described in previous examples of oligonucleotide array hybridization), the relative level of label (from stacking probes) bound to each color-coded bead will provide a gene expression (transcriptional) profile. The stacking probe must be labeled with a tag that is distinguishable from the spectral properties of color-coded beads. If dual labels are used (one used in preannealing with a "reference" sample and another used in preannealing with a "test" sample, and the two samples are hybridized together with the mixture of color-coded beads, the relative binding of the two labels (from stacking probes) to each color-coded bead will reveal the two transcriptional profiles simulaneously. As in Example 16, universal stacking probes (targeted to polyA tail or mRNA (or polyT of cDNA) or to repetitive sequence elements within genomic DNA, may be employed with bead technology to achieve transcriptional profiling or genotyping, respectively. FIG. 15B shows an alternative embodiment of the tandem hybridization approach on beads. Here, the capture probes tethered to color-coded beads are of sequence and length necessary to bind uniquely to the desired regions of the analyte nucleic acid. The mixture of bead-tethered capture probes are mixed with the analyte nucleic acid along with short labeled sequence-specific oligonucleotide probes, each designed to hybridize in tandem with a specific capture probe. For gene expression profiling, each expressed sequence is represented by a specific capture probe tethered to a color-coded bead, plus a labeled probe which hybridizes in tandem with the capture probe. Thus, the level of label (from the shorter probe) bound to each color-coded bead (through contiguous stacking between longer capture probe and shorter labeled probe) will reveal the transcriptional profile. As in the example of FIG. 15A, a two-color system of short probes may be used to compare reference and test transcriptional profiles. Similarly, for genotyping and mutational analysis, each polymorphic marker is represented by a sequence specific longer capture probe designed to stack contiguously with a shorter labeled probe (when hybridized with the DNA analyte) or with a number of allele-specific labeled probes. The level of each label (from the shorter labeled probes) bound to each color-coded bead will then reveal the allelic status at each polymorphic or mutation-bearing site. A high degree of multiplexing (enabling simultaneous analysis of numerous target sequences) is provided by the use of color-coded beads in the FlowMetrix system, for example thousands of different color codes can be distinguished using several fluorescent dyes mixed together in defined ratios at different levels, providing a large number of distinct spectral profiles. As discussed above, the tandem hybridization approach can be used with bead technology as long as the labels associated with the stacking probes are distinguishable from those of the "coded" beads, and a wide variety of physical or chemical properties may be incorporated into the microspheres to enable alternative bead-identifying detection schemes.

What is claimed is:

1. A method for analyzing nucleic acids comprising the steps of:

preparing a target nucleic acid/labeled probe mixture by mixing a heat-denatured nucleic acid sample comprising a target nucleic acid with a molar excess of one or more labeled probes wherein said labeled probes are oligonucleotides with lengths and sequences selected for optimal annealing to unique positions within the target nucleic acid;

hybridizing said target nucleic acid/labeled probe mixture to an array of surface-tethered capture probes wherein said capture probes are oligonucleotides designed to anneal to the target nucleic acid in tandem with at least one of said labeled probes, wherein said capture probes are surface-tethered at one end to a specific region of a solid phase support material, and wherein hybridization conditions are selected such that a capture probe from said array can bind to said target nucleic acid only when hybridized in tandem with at least one labeled probe, forming stable, contiguously stacked labeled probe/capture probe duplex structures containing no base mismatches at or near the junctions of said labeled probes and said capture probes; and analyzing the resulting pattern of binding of label across the surface of said solid phase support material to reveal the presence of sequences in the target nucleic acid complementary to tandemly hybridized complexes of said labeled probes and said capture probes.

2. The method of claim 1, wherein said target nucleic acid/labeled probe mixture is preannealed and incubated under stringent hybridization conditions to enable binding of said labeled probes to unique positions within the nucleic acid sample, prior to hybridization of said mixture to said array of surface-tethered capture probes.

3. The method of claim 2, wherein said stringent hybridization conditions are near the Tm of the duplex structures of the labeled and capture probes.

4. The method of claim 1, wherein said target nucleic acid/labeled probe mixture is applied directly to said array of surface-tethered capture probes and incubated under hybridization conditions permitting said labeled probes to bind specifically to complementary sequences within the nucleic acid sample, wherein said surface-tethered capture probes form a stable duplex structure with the target nucleic acid only if said surface-tethered capture probes hybridize in tandem with said labeled probes.

5. The method of claim 1, wherein probes selected from the group consisting of the labeled probes and the capture probes contain 5'-phosphate groups.

6. The method of claim 5, wherein said labeled probes and said capture probes are covalently joined by means of an enzymatic reaction catalyzed by DNA ligase and wherein said labeled probes and said capture probes are not stabilized through hybridization and said labeled probes are not washed from the oligonucleotide array at elevated temperatures.

7. The method of claim 1, wherein two or more labeled probes are designed to hybridize to the target nucleic acid in the region to which the capture probe hybridizes, and wherein said labeled probes are mixed in molar excess with the heat-denatured nucleic acid sample to form a bubble structure, wherein said bubble structure has improved accessibility to hybridization with the capture probe, and, wherein said bubble structure inhibits the formation of interfering interstrand or intrastrand secondary structure at the site of hybridization of capture probe with the target strand.

8. The method of claim 1, wherein said solid phase support material is selected from the group consisting of glass, silicon, silicon dioxide, ceramic, plastic, latex, metal and metal oxide.

9. The method of claim 8, wherein said solid phase support material comprises a flowthrough porous layer selected from the group consisting of glass fiber filters, etched silicon structures, microchannel glass, micromachined ceramics, porous plastics, and metal oxide membranes.

10. The method of claim 1, wherein one or more of said labeled probes have lengths of 6–50 nucleotides and said surface-tethered capture probes have lengths of 5–15 nucleotides.

11. The method of claim 1, wherein said labeled probes and said surface-tethered capture probes are selected to be complementary to known, unique nucleotide sequences within the target nucleic acid, wherein sequences corresponding to Alu, LINE, SINE and other repetitive genomic sequence elements are excluded from said labeled probes and from said capture probes.

12. The method of claim 1, wherein said surface-tethered capture probes and said labeled probes represent a collection of known sequence variations within regions of the nucleic acid target complementary to the labeled probes and the capture probes, wherein a quantitative pattern of binding of label to the array of surface-tethered capture probes reveals sequence variations identifying an allele and whether said nucleic acid target is homozygous or heterozygous for said allele.

13. The method of claim 1, wherein said surface-tethered capture probes and said labeled probes represent a collection of sequences unique for known genomic sequences, wherein a quantitative pattern of binding of label to the array of surface-tethered capture probes reveals the presence and/or relative abundance of known species, strains or subtypes in a biological sample from which said nucleic acid sample is derived.

14. The method of claim 1, wherein said surface-tethered capture probes and said labeled probes represent a collection of sequences unique for known expressed gene sequences, wherein a quantitative pattern of binding of label to the array of surface-tethered capture probes reveals the relative transcription levels among different genes.

15. The method of claim 1, wherein a label is introduced into an oligonucleotide to form the labeled probe by a means selected from the group consisting of polynucleotide kinase catalysis, DNA polymerase catalysis, terminal deoxynucleotidyltransferase catalysis, and incorporation of at least one labeled residue during chemical synthesis of the oligonucleotide.

16. The method of claim 1, wherein said labeled probes comprise a label selected from the group consisting of a radioactive tag, a fluorescent tag, a chemiluminescent tag, a tag of unique molecular structure, identifiable by mass spectroscopy, a protein tag, an enzymatic tag, and a ligand.

17. The method of claim 16, wherein multiplex nucleic acid sequence analysis is enabled via the use of specific mixtures of distinguishable labeled probes, each being targeted to a unique sequence in the nucleic acid sample and each containing a single distinguishable label.

18. The method of claim 16, wherein multiplex nucleic acid sequence analysis is enabled via the use of a mixture of labels of distinguishable composition, selected to specify a unique, identifiable signature for each of said labeled probes.

19. A method for directly analyzing sequence variations between two or more samples of genomic DNA, comprising the steps of:
extracting a first extracted genomic DNA sample from a first biological sample;
preparing a first genomic DNA/labeled probe mixture by heat-denaturing said first genomic DNA sample and mixing it with a molar excess of one or more labeled probes, the length and sequence of each labeled probe selected to permit annealing at a unique position within the genome;
hybridizing said first genomic DNA labeled probe mixture to an array of end-tethered capture probes selected to hybridize in tandem with said labeled probes, the hybridization conditions selected such that an individual capture probe can bind to a genomic DNA strand only if it hybridizes to the genomic DNA target in tandem with a labeled probe;
acquiring a quantitative hybridization pattern for said first genomic DNA/labeled probe mixture;
extracting a second extracted genomic DNA sample from a second biological sample;
preparing a second genomic DNA/labeled probe mixture by heat-denaturing and mixing said second genomic DNA sample with a molar excess of one or more labeled probes, the length and sequence of each labeled probe selected to permit annealing at a unique position within the genome;
hybridizing said second genomic DNA/labeled probe mixture to an array of end-tethered capture probes selected to hybridize in tandem with said labeled probes, the hybridization conditions selected such that the capture probes cannot form stable hybrids with the genomic DNA unless they hybridize in tandem with labeled probes on the genomic DNA target;
acquiring a quantitative hybridization pattern for said second genomic DNA/labeled probe mixture; and
comparing the quantitative hybridization patterns obtained from said first, said second, and any additional genomic DNA samples, to reveal the allele status, i.e., wild-type, mutant or polymorphic variation, and homozygous or heterozygous condition at each of the sites of sequence variation in the genomic DNA, represented by the tandemly hybridizing labeled and capture probes.

20. A method for directly analyzing and comparing patterns of gene expression at the level of transcription in different cellular samples, comprising the steps of:
isolating a first preparation of expressed sequences from a first biological sample, wherein said isolation is by extraction of cellular mRNA or by conversion of extracted cellular RNA to cDNA using reverse transcriptase;
preparing a first mixture of expressed sequences and labeled probes by heat-denaturing said first preparation of expressed sequences and mixing it with one or more labeled probes in molar excess over said expressed sequences, the length and sequence of each labeled probe selected to permit annealing at a unique position within the expressed sequences;
hybridizing said first mixture of expressed sequences and labeled probe(s) to an array of end-tethered capture probes selected to hybridize to expressed sequences in tandem with said labeled probes;
acquiring a quantitative hybridization pattern for said first preparation of expressed sequences;
comparing quantitative binding of said first mixture of expressed sequences and labeled probe(s) at different sites within said array of end-tethered capture probes, to reveal the relative abundance of different gene transcripts within said first biological sample;
isolating a second preparation of expressed sequences from a second biological sample;
preparing a second mixture of expressed sequences and labeled probe(s) by heat-denaturing said second preparation of expressed sequences and mixing it with one or more labeled probes in molar excess over said expressed sequences, the length and sequence of each labeled probe selected to permit annealing at a unique position within the expressed sequences;
hybridizing said second mixture of expressed sequences and labeled probe(s) to an array of end-tethered capture probes selected to hybridize to expressed sequences in tandem with said labeled probes;

acquiring a quantitative hybridization pattern for said second preparation of expressed sequences;

comparing quantitative binding of said second mixture of expressed sequences and labeled probe(s) at different sites within said array of end-tethered capture probes, to reveal the relative abundance of different gene transcripts within said second biological sample; and comparing the quantitative hybridization patterns obtained from said first preparations of expressed sequences, second preparations of expressed sequences, and any additional preparations of expressed sequences, to reveal the relative abundance of gene transcripts in different biological samples.

21. The method of claim 20, wherein each analyzed expressed sequence is represented by a unique pair of tandemly hybridizing capture probe and labeled probe, targeted to a unique nucleotide sequence in each mRNA.

22. The method of claim 20, wherein a universal labeled probe anneals to the poly(A) sequence adjacent to the 3'-untranslated region of any polyadenylated mRNA, or to the corresponding poly(dT) region of cDNA, and wherein each analyzed expressed sequence hybridizes to a unique capture probe in tandem with the universal labeled probe.

23. The method of claim 20, wherein said labeled probes anneal to mRNA or cDNA in the region comprising the 3'-poly(A) tails of mRNA or to the corresponding 5'-poly (dT) tails of cDNA, respectively, plus 1–5 nucleotides of mRNA or cDNA immediately adjacent to said poly(A) or poly(dT) tail, and whereas the array of capture probes comprises a complete collection of all possible 5 mer, 6 mer or 7 mer oligonucleotides or a substantial subset thereof.

* * * * *

SEQUENCE LISTING

```
<160> NUMBER OF SEQ ID NOS: 55

<210> SEQ ID NO: 1
<211> LENGTH: 138
<212> TYPE: DNA
<213> ORGANISM: artificial sequence
<220> FEATURE:
<223> OTHER INFORMATION: fragment derived from exon 10 in the CFTR gene
      containing cystic fibrosis mutation sites Q493X,
      ΔI507, ΔF508, and ΔV520F

<400> SEQUENCE: 1
gcacagtgga agaatttcat tctgttctca gttttcctgg attatgcctg          50
gcaccattaa agaaaatatc atctttggtg tttcctatga tgaatataga         100
tacagaagcg tcatcaaagc atgccaagta gaagaggt                      138

<210> SEQ ID NO: 2
<211> LENGTH: 24
<212> TYPE: DNA
<213> ORGANISM: artificial sequence
<220> FEATURE:
<221> NAME/KEY: primer
<223> OTHER INFORMATION: CF163 primer used to amplify a 138 base pair
      fragment derived from exon 10 in the CFTR gene

<400> SEQUENCE: 2
gcacagtgga agaatttcat tctg                                      24
```

<210> SEQ ID NO: 3
<211> LENGTH: 24
<212> TYPE: DNA
<213> ORGANISM: artificial sequence
<220> FEATURE:
<221> NAME/KEY: primer
<223> OTHER INFORMATION: CF164 primer used to amplify a 138 base pair
      fragment derived from exon 10 in the CFTR gene;
      also, used as an auxiliary oligonucleotide

<400> SEQUENCE: 3
acctcttcta gttggcatgc tttg                                          24

<210> SEQ ID NO: 4
<211> LENGTH: 20
<212> TYPE: DNA
<213> ORGANISM: artificial sequence
<220> FEATURE:
<223> OTHER INFORMATION: CF168 auxiliary oligonucleotide produces
      partially duplex structure across target sequence; anneals to
      138 base PCR product from exon 10 of CFTR gene

<400> SEQUENCE: 4
atgaaattct tccactgttc                                               20

<210> SEQ ID NO: 5
<211> LENGTH: 30
<212> TYPE: DNA
<213> ORGANISM: artificial sequence
<220> FEATURE:
<223> OTHER INFORMATION: CF169 auxiliary oligonucleotide produces
      partially duplex structure across target sequence; anneals to
      138 base PCR product from exon 10 of CFTR gene

<400> SEQUENCE: 5
ttctttaatg gtgccaggca taatccagga                                    30

<210> SEQ ID NO: 6
<211> LENGTH: 22
<212> TYPE: DNA
<213> ORGANISM: artificial sequence
<220> FEATURE:
<223> OTHER INFORMATION: CF170 auxiliary oligonucleotide produces
      partially duplex structure across target sequence; anneals to
      138 base PCR product from exon 10 of CFTR gene

<400> SEQUENCE: 6
gtatctatat tcatcatagg aa                                            22

<210> SEQ ID NO: 7
<211> LENGTH: 9
<212> TYPE: DNA
<213> ORGANISM: artificial sequence
<220> FEATURE:
<223> OTHER INFORMATION: CF10W probe hybridizes with Q493X mutation
      site; the 5'terminal adenosine is derivatized to carry
      a primary amino group which covalently binds to the
      epoxysilanized glass

<400> SEQUENCE: 7 actgagaac                                                            9

<210> SEQ ID NO: 8
<211> LENGTH: 9
<212> TYPE: DNA
<213> ORGANISM: artificial sequence
<220> FEATURE:

```
<223> OTHER INFORMATION: CF10M probe hybridizes with Q493X mutation
      site; the 5'terminal thymidine is derivatized to carry
      a primary amino group which covalently binds to the
      epoxysilanized glass

<400> SEQUENCE: 8 taagaacag                                                              9

<210> SEQ ID NO: 9
<211> LENGTH: 9
<212> TYPE: DNA
<213> ORGANISM: artificial sequence
<220> FEATURE:
<223> OTHER INFORMATION: CF11W probe hybridizes with ΔI507 mutation
      site; the 5'terminal adenosine is derivatized to carry
      a primary amino group which covalently binds to the
      epoxysilanized glass

<400> SEQUENCE: 9 aagatgata                                                              9

<210> SEQ ID NO: 10
<211> LENGTH: 9
<212> TYPE: DNA
<213> ORGANISM: artificial sequence
<220> FEATURE:
<223> OTHER INFORMATION: CF11M probe hybridizes with ΔI507 mutation
      site; the 5'terminal cytidine is derivatized to carry
      a primary amino group which covalently binds to the
      epoxysilanized glass

<400> SEQUENCE: 10 ccaaagata                                                              9

<210> SEQ ID NO :11
<211> LENGTH: 9
<212> TYPE: DNA
<213> ORGANISM: artificial sequence
<220> FEATURE:
<223> OTHER INFORMATION: CF12W probe hybridizes with ΔF508 mutation
      site; the 5'terminal cytidine is derivatized to carry
      a primary amino group which covalently binds to the
      epoxysilanized glass

<400> SEQUENCE: 11 ccaaagatg                                                              9

<210> SEQ ID NO: 12
<211> LENGTH: 9
<212> TYPE: DNA
<213> ORGANISM: artificial sequence
<220> FEATURE:
<223> OTHER INFORMATION: CF12M probe hybridizes with ΔF508 mutation
      site; the 5'terminal cytidine is derivatized to carry
      a primary amino group which covalently binds to the
      epoxysilanized glass

<400> SEQUENCE: 12 caccgatga                                                              9

<210> SEQ ID NO: 13
<211> LENGTH: 9
<212> TYPE: DNA
<213> ORGANISM: artificial sequence
<220> FEATURE:
<223> OTHER INFORMATION: CF13W probe hybridizes with V520F mutation
      site; the 5'terminal adenosine is derivatized to carry
      a primary amino group which covalently binds to the
      epoxysilanized glass
```

<400> SEQUENCE: 13 atgacgctt                                                                  9

<210> SEQ ID NO: 14
<211> LENGTH: 9
<212> TYPE: DNA
<213> ORGANISM: artificial sequence
<220> FEATURE:
<223> OTHER INFORMATION: CF13M probe hybridizes with V520F mutation
      site; the 5'terminal guanidine is derivatized to carry
      a primary amino group which covalently binds to the
      epoxysilanized glass

<400> SEQUENCE: 14 gatgaagct                                                                  9

<210> SEQ ID NO: 15
<211> LENGTH: 9
<212> TYPE: DNA
<213> ORGANISM: artificial sequence
<220> FEATURE:
<223> OTHER INFORMATION: CFW13 probe; the 3'terminal thymidine contains
      an aminopropanol which covalently binds to
      the epoxysilanized glass

<400> SEQUENCE: 15 atgacgctt                                                                  9

<210> SEQ ID NO: 16
<211> LENGTH: 9
<212> TYPE: DNA
<213> ORGANISM: artificial sequence
<220> FEATURE:
<223> OTHER INFORMATION: CF195 probe; the 3'terminal thymidine contains
      an aminopropanol which covalently binds to
      the epoxysilanized glass

<400> SEQUENCE: 16 ttgacgctt                                                                  9

<210> SEQ ID NO: 17
<211> LENGTH: 9
<212> TYPE: DNA
<213> ORGANISM: artificial sequence
<220> FEATURE:
<223> OTHER INFORMATION: CF196 probe; the 3'terminal thymidine contains
      an aminopropanol which covalently binds to
      the epoxysilanized glass

<400> SEQUENCE: 17 ctgacgctt                                                                  9

<210> SEQ ID NO: 18
<211> LENGTH: 9
<212> TYPE: DNA
<213> ORGANISM: artificial sequence
<220> FEATURE:
<223> OTHER INFORMATION: CF197 probe; the 3'terminal thymidine contains
      an aminopropanol which covalently binds to
      the epoxysilanized glass

<400> SEQUENCE: 18 gtgacgctt                                                                  9

<210> SEQ ID NO: 19
<211> LENGTH: 9

```
<212> TYPE: DNA
<213> ORGANISM: artificial sequence
<220> FEATURE:
<223> OTHER INFORMATION: CFW13-P probe; the 5' terminal adenosine is
      phosphorylated and the 3' terminal thymidine
      contains an aminopropanol which covalently binds
      to the epoxysilanized glass

<400> SEQUENCE: 19 atgacgctt                                                                    9

<210> SEQ ID NO: 20
<211> LENGTH: 9
<212> TYPE: DNA
<213> ORGANISM: artificial sequence
<220> FEATURE:
<223> OTHER INFORMATION: CF195-P probe; the 5' terminal thymidine is
      phosphorylated and the 3' terminal thymidine
      contains an aminopropanol which covalently binds
      to the epoxysilanized glass

<400> SEQUENCE: 20 ttgacgctt                                                                    9

<210> SEQ ID NO: 21
<211> LENGTH: 9
<212> TYPE: DNA
<213> ORGANISM: artificial sequence
<220> FEATURE:
<223> OTHER INFORMATION: CF196-P probe; the 5' terminal cytidine is
      phosphorylated and the 3' terminal thymidine
      contains an aminopropanol which covalently binds
      to the epoxysilanized glass

<400> SEQUENCE: 21 ctgacgctt                                                                    9

<210> SEQ ID NO: 22
<211> LENGTH: 9
<212> TYPE: DNA
<213> ORGANISM: artificial sequence
<220> FEATURE:
<223> OTHER INFORMATION: CF197-F probe; the 5' terminal guanosine is
      phosphorylated and the 3' terminal thymidine
      contains an aminopropanol which covalently binds
      to the epoxysilanized glass

<400> SEQUENCE: 22 gtgacgctt                                                                    9

<210> SEQ ID NO: 23
<211> LENGTH: 8
<212> TYPE: DNA
<213> ORGANISM: artificial sequence
<220> FEATURE:
<223> OTHER INFORMATION: CFW13-8 probe; the 3'terminal thymidine
      contains an aminopropanol which covalently binds to
      the epoxysilanized glass

<400> SEQUENCE: 23 atgacgct                                                                     8

<210> SEQ ID NO: 24
<211> LENGTH: 8
<212> TYPE: DNA
<213> ORGANISM: artificial sequence
<220> FEATURE:
<223> OTHER INFORMATION: CF195-8 probe; the 3'terminal thymidine
      contains an aminopropanol which covalently binds to
``` the epoxysilanized glass

<400> SEQUENCE: 24 ttgacgct                                                                  8

<210> SEQ ID NO: 25
<211> LENGTH: 8
<212> TYPE: DNA
<213> ORGANISM: artificial sequence
<220> FEATURE:
<223> OTHER INFORMATION: CF196-8 probe; the 3'terminal thymidine
      contains an aminopropanol which covalently binds to
      the epoxysilanized glass

<400> SEQUENCE: 25 ctgacgct                                                                  8

<210> SEQ ID NO: 26
<211> LENGTH: 8
<212> TYPE: DNA
<213> ORGANISM: artificial sequence
<220> FEATURE:
<223> OTHER INFORMATION: CF197-8 probe; the 3'terminal thymidine
      contains an aminopropanol which covalently binds to
      the epoxysilanized glass

<400> SEQUENCE: 26 gtgacgct                                                                  8

<210> SEQ ID NO: 27
<211> LENGTH: 7
<212> TYPE: DNA
<213> ORGANISM: artificial sequence
<220> FEATURE:
<223> OTHER INFORMATION: CFW13-7 probe; the 3'terminal cytidine contains
      an aminopropanol which covalently binds to
      the epoxysilanized glass

<400> SEQUENCE: 27 atgacgc                                                                   7

<210> SEQ ID NO: 28
<211> LENGTH: 7
<212> TYPE: DNA
<213> ORGANISM: artificial sequence
<220> FEATURE:
<223> OTHER INFORMATION: CF195-7 probe; the 3'terminal cytidine contains
      an aminopropanol which covalently binds to
      the epoxysilanized glass

<400> SEQUENCE: 28 ttgacgc                                                                   7

<210> SEQ ID NO: 29
<211> LENGTH: 7
<212> TYPE: DNA
<213> ORGANISM: artificial sequence
<220> FEATURE:
<223> OTHER INFORMATION: CF196-7 probe; the 3'terminal cytidine contains
      an aminopropanol which covalently binds to
      the epoxysilanized glass

<400> SEQUENCE: 29 ctgacgc                                                                   7

<210> SEQ ID NO: 30
<211> LENGTH: 7

```
<212> TYPE: DNA
<213> ORGANISM: artificial sequence
<220> FEATURE:
<223> OTHER INFORMATION: CF197-7 probe; the 3'terminal cytidine contains
      an aminopropanol which covalently binds to
      the epoxysilanized glass

<400> SEQUENCE: 30 gtgacgc                                                                    7

<210> SEQ ID NO: 31
<211> LENGTH: 6
<212> TYPE: DNA
<213> ORGANISM: artificial sequence
<220> FEATURE:
<223> OTHER INFORMATION: CFW13-6 probe; the 3'terminal guanidine
      contains an aminopropanol which covalently binds to
      the epoxysilanized glass

<400> SEQUENCE: 31 atgacg                                                                     6

<210> SEQ ID NO: 32
<211> LENGTH: 6
<212> TYPE: DNA
<213> ORGANISM: artificial sequence
<220> FEATURE:
<223> OTHER INFORMATION: CF195-6 probe; the 3'terminal guanidine
      contains an aminopropanol which covalently binds to
      the epoxysilanized glass

<400> SEQUENCE: 32 ttgacg                                                                     6

<210> SEQ ID NO: 33
<211> LENGTH: 6
<212> TYPE: DNA
<213> ORGANISM: artificial sequence
<220> FEATURE:
<223> OTHER INFORMATION: CF196-6 probe; the 3'terminal guanidine
      contains an aminopropanol which covalently binds to
      the epoxysilanized glass

<400> SEQUENCE: 33 ctgacg                                                                     6

<210> SEQ ID NO: 34
<211> LENGTH: 6
<212> TYPE: DNA
<213> ORGANISM: artificial sequence
<220> FEATURE:
<223> OTHER INFORMATION: CF197-6 probe; the 3'terminal guanidine
      contains an aminopropanol which covalently binds to
      the epoxysilanized glass

<400> SEQUENCE: 34 gtgacg                                                                     6

<210> SEQ ID NO: 35
<211> LENGTH: 34
<212> TYPE: DNA
<213> ORGANISM: artificial sequence
<220> FEATURE:
<223> OTHER INFORMATION: CF179 synthetic target

<400> SEQUENCE: 35
agaagcttca tcaaagcatg ccaactagaa gagg                                     34
```

```
<210> SEQ ID NO: 36
<211> LENGTH: 34
<212> TYPE: DNA
<213> ORGANISM: artificial sequence
<220> FEATURE:
<223> OTHER INFORMATION: CF180 synthetic target

<400> SEQUENCE: 36
agaagcttca gcaaagcatg ccaactagaa gagg                                 34

<210> SEQ ID NO: 37
<211> LENGTH: 34
<212> TYPE: DNA
<213> ORGANISM: artificial sequence
<220> FEATURE:
<223> OTHER INFORMATION: CF181 synthetic target

<400> SEQUENCE: 37
agaagcttca ccaaagcatg ccaactagaa gagg                                 34

<210> SEQ ID NO: 38
<211> LENGTH: 34
<212> TYPE: DNA
<213> ORGANISM: artificial sequence
<220> FEATURE:
<223> OTHER INFORMATION: CF182 synthetic target

<400> SEQUENCE: 38
agaagcttca acaaagcatg ccaactagaa gagg                                 34

<210> SEQ ID NO: 39
<211> LENGTH: 34
<212> TYPE: DNA
<213> ORGANISM: artificial sequence
<220> FEATURE:
<223> OTHER INFORMATION: CF179-7G synthetic target

<400> SEQUENCE: 39
agaagcgtca tcaaagcatg ccaactagaa cagg                                 34

<210> SEQ ID NO: 40
<211> LENGTH: 34
<212> TYPE: DNA
<213> ORGANISM: artificial sequence
<220> FEATURE:
<223> OTHER INFORMATION: CF180-7G   synthetic target

<400> SEQUENCE: 40
agaagcgtca gcaaagcatg ccaactagaa gagg                                 34

<210> SEQ ID NO: 41
<211> LENGTH: 34
<212> TYPE: DNA
<213> ORGANISM: artificial sequence
<220> FEATURE:
<223> OTHER INFORMATION: CF181-7G   synthetic target

<400> SEQUENCE: 41
agaagcgtca ccaaagcatg ccaactagaa cagg                                 34

<210> SEQ ID NO: 42
<211> LENGTH: 34
<212> TYPE: DNA
<213> ORGANISM: artificial sequence
<220> FEATURE:
<223> OTHER INFORMATION: CF182-7G synthetic target
```

-continued

<400> SEQUENCE: 42
agaagcgtca acaaagcatg ccaactagaa gagg                              34

<210> SEQ ID NO: 43
<211> LENGTH: 7
<212> TYPE: DNA
<213> ORGANISM: artificial sequence
<220> FEATURE:
<223> OTHER INFORMATION: CF198 probe; the 3'terminal cytidine contains
      an aminopropanol which covalently binds to
      the epoxysilanized glass

<400> SEQUENCE: 43 aagacgc                                                            7

<210> SEQ ID NO: 44
<211> LENGTH: 7
<212> TYPE: DNA
<213> ORGANISM: artificial sequence
<220> FEATURE:
<223> OTHER INFORMATION: CF199 probe; the 3'terminal cytidine contains
      an aminopropanol which covalently binds to
      the epoxysilanized glass

<400> SEQUENCE: 44 acgacgc                                                            7

<210> SEQ ID NO: 45
<211> LENGTH: 7
<212> TYPE: DNA
<213> ORGANISM: artificial sequence
<220> FEATURE:
<223> OTHER INFORMATION: CF200 probe; the 3'terminal cytidine contains
      an aminopropanol which covalently binds to
      the epoxysilanized glass

<400> SEQUENCE: 45 aggacgc                                                            7

<210> SEQ ID NO: 46
<211> LENGTH: 7
<212> TYPE: DNA
<213> ORGANISM: artificial sequence
<220> FEATURE:
<223> OTHER INFORMATION: CF201 probe; the 3'terminal cytidine contains
      an aminopropanol which covalently binds to
      the epoxysilanized glass

<400> SEQUENCE: 46 ataacgc                                                            7

<210> SEQ ID NO: 47
<211> LENGTH: 7
<212> TYPE: DNA
<213> ORGANISM: artificial sequence
<220> FEATURE:
<223> OTHER INFORMATION: CF202 probe; the 3'terminal cytidine contains
      an aminopropanol which covalently binds to
      the epoxysilanized glass

<400> SEQUENCE: 47 atcacgc                                                            7

<210> SEQ ID NO: 48
<211> LENGTH: 7
<212> TYPE: DNA

```
<213> ORGANISM: artificial sequence
<220> FEATURE:
<223> OTHER INFORMATION: CF203 probe; the 3'terminal cytidine contains
      an aminopropanol which covalently binds to
      the epoxysilanized glass

<400> SEQUENCE: 48 attacgc                                                              7

<210> SEQ ID NO: 49
<211> LENGTH: 7
<212> TYPE: DNA
<213> ORGANISM: artificial sequence
<220> FEATURE:
<223> OTHER INFORMATION: CF204 probe; the 3'terminal cytidine contains
      an aminopropanol which covalently binds to
      the epoxysilanized glass

<400> SEQUENCE: 49 atgccgc                                                              7

<210> SEQ ID NO: 50
<211> LENGTH: 7
<212> TYPE: DNA
<213> ORGANISM: artificial sequence
<220> FEATURE:
<223> OTHER INFORMATION: CF205 probe; the 3'terminal cytidine contains
      an aminopropanol which covalently binds to
      the epoxysilanized glass

<400> SEQUENCE: 50 atggcgc                                                              7

<210> SEQ ID NO: 51
<211> LENGTH: 7
<212> TYPE: DNA
<213> ORGANISM: artificial sequence
<220> FEATURE:
<223> OTHER INFORMATION: CF206 probe; the 3'terminal cytidine contains
      an aminopropanol which covalently binds to
      the epoxysilanized glass

<400> SEQUENCE: 51 atgtcgc                                                              7

<210> SEQ ID NO: 52
<211> LENGTH: 7
<212> TYPE: DNA
<213> ORGANISM: artificial sequence
<220> FEATURE:
<223> OTHER INFORMATION: CF207 probe; the 3'terminal cytidine contains
      an aminopropanol which covalently binds to
      the epoxysilanized glass

<400> SEQUENCE: 52 atgaggc                                                              7

<210> SEQ ID NO: 53
<211> LENGTH: 7
<212> TYPE: DNA
<213> ORGANISM: artificial sequence
<220> FEATURE:
<223> OTHER INFORMATION: CF208 probe; the 3'terminal cytidine contains
      an aminopropanol which covalently binds to
      the epoxysilanized glass

<400> SEQUENCE: 53 atgatgc                                                              7
```

```
<210> SEQ ID NO: 54
<211> LENGTH: 7
<212> TYPE: DNA
<213> ORGANISM: artificial sequence
<220> FEATURE:
<223> OTHER INFORMATION: CF209 probe; the 3'terminal cytidine contains
      an aminopropanol which covalently binds to
      the epoxysilanized glass

<400> SEQUENCE: 54 atgaagc                                                              7

<210> SEQ ID NO: 55
<211> LENGTH: 30
<212> TYPE: DNA
<213> ORGANISM: artificial sequence
<220> FEATURE:
<223> OTHER INFORMATION: Sequence of CFW13 capture probe hybridized
      with CF164 stacking probe

<400> SEQUENCE: 55
cctcttctag ttggcatgct ttgatgacgc                                    30
```